United States Patent
Hirano et al.

(10) Patent No.: US 9,932,614 B2
(45) Date of Patent: Apr. 3, 2018

(54) METHOD FOR PRODUCING L-AMINO ACID OF GLUTAMATE FAMILY

(71) Applicant: AJINOMOTO CO., INC., Tokyo (JP)

(72) Inventors: Seiko Hirano, Kanagawa (JP); Kazuyuki Hayashi, Kanagawa (JP); Hitoshi Takayashiki, Kanagawa (JP); Keita Fukui, Kanagawa (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 15/334,444

(22) Filed: Oct. 26, 2016

(65) Prior Publication Data

US 2017/0121743 A1   May 4, 2017

(30) Foreign Application Priority Data

Oct. 30, 2015  (JP) .................. 2015-215052

(51) Int. Cl.
| | | |
|---|---|---|
| *C12P 13/14* | (2006.01) | |
| *C12N 1/20* | (2006.01) | |
| *C12N 15/70* | (2006.01) | |
| *C12N 15/77* | (2006.01) | |
| *C07K 14/34* | (2006.01) | |
| *C12P 13/10* | (2006.01) | |
| *C12P 13/24* | (2006.01) | |

(52) U.S. Cl.
CPC .............. *C12P 13/14* (2013.01); *C07K 14/34* (2013.01); *C12P 13/10* (2013.01); *C12P 13/24* (2013.01)

(58) Field of Classification Search
None
See application file for complete search history.

(56) References Cited

U.S. PATENT DOCUMENTS

| 8,628,941 | B2 | 1/2014 | Fukui et al. |
| 9,080,189 | B2 | 7/2015 | Fukui et al. |
| 2012/0040415 | A1 | 2/2012 | Nakahara et al. |
| 2015/0259717 | A1 | 9/2015 | Hara et al. |
| 2015/0307907 | A1 | 10/2015 | Hirano et al. |
| 2016/0130618 | A1 | 5/2016 | Hara et al. |

FOREIGN PATENT DOCUMENTS

| WO | WO01/05959 A1 | 1/2001 |
| WO | WO2006/015705 A1 | 2/2006 |
| WO | WO2006/070944 A2 | 7/2006 |

OTHER PUBLICATIONS

Seol, W., et al., "*Escherichia coli* kgtP encodes an α-ketoglutarate transporter," Proc. Natl. Acad. Sci. USA 1991;88:3802-3806.
Schneider, J., et al., "Production of the amino acids L-glutamate, L-lysine, L-ornithine and L-arginine from arabinose by recombinant Corynebacterium glutamicum," J. Biotechnol. 2011;154:191-198.
European Search Report for EP Patent App. No. 16196254.3 dated Apr. 10, 2017.

*Primary Examiner* — Iqbal H Chowdhury
(74) *Attorney, Agent, or Firm* — Cermak Nakajima & McGowan LLP; Shelly Guest Cermak

(57) ABSTRACT

A method for producing an L-amino acid of glutamate family such as L-glutamic acid is provided. An L-amino acid of glutamate family is produced by culturing a coryneform bacterium having an ability for producing an L-amino acid of glutamate family, which has been modified so that the activity of an α-ketoglutaric acid (α-KG) uptake carrier is increased, in a medium, and collecting the L-amino acid of glutamate family from the medium.

17 Claims, No Drawings

US 9,932,614 B2

METHOD FOR PRODUCING L-AMINO ACID OF GLUTAMATE FAMILY

This application claims priority under 35 U.S.C. § 119 to Japanese Patent Application No. 2015-215052, filed Oct. 30, 2015, the entirety of which is incorporated by reference herein. Also, the Sequence Listing filed electronically herewith is hereby incorporated by reference (File name: 2016-10-26T_US-550_Seq_List; File size: 36 KB; Date recorded: Oct. 26, 2016).

BACKGROUND OF THE INVENTION

Field of the Invention

The present invention relates to a method for producing an L-amino acid of the glutamate family, such as L-glutamic acid, using a coryneform bacterium. L-amino acids are industrially useful as raw materials in the production of seasonings, and so forth.

Brief Description of the Related Art

L-amino acids are industrially produced by, for example, fermentation using microorganisms such as coryneform bacteria that are able to produce L-amino acids (Akashi, K. et al., Amino Acid Fermentation. Japan Scientific Societies Press, p. 195 to 215, 1986). As such microorganisms, for example, strains isolated from nature, and mutant strains thereof, have been used. Also, the ability of these microorganisms to produce L-amino acids can be improved by using recombinant DNA techniques. Such techniques include, for example, enhancing phosphoketolase activity (WO2006/016705) or using a mutant yggB gene (WO2006/070944).

The kgtP gene of *Escherichia coli* encodes an α-ketoglutaric acid (α-KG) uptake carrier (Seol W, Shatkin A J. *Escherichia coli* kgtP encodes an alpha-ketoglutarate transporter. Proc Natl Acad Sci USA. 1991 May 1; 88(9):3802-6). α-KG is known to be an intermediate in the biosynthesis of L-glutamic acid. However, the relationship between an α-KG uptake carrier and production of L-amino acids of glutamate family has not been previously reported.

SUMMARY OF THE INVENTION

It is an aspect of the present invention to develop a novel technique for improving the ability of a coryneform bacterium to produce L-amino acids of the glutamate family, and thereby provide a method for efficiently producing L-amino acids of glutamate family.

It has been found that the ability of a coryneform bacterium to produce L-amino acids of the glutamate family can be improved by modifying the coryneform bacterium so that the activity of an α-ketoglutaric acid (α-KG) uptake carrier is increased.

It is an aspect of the present invention to provide a method for producing an L-amino acid, the method comprising culturing a coryneform bacterium having an L-amino acid-producing ability in a medium; and collecting the L-amino acid from the medium, wherein the bacterium has been modified so that the activity of an α-ketoglutaric acid (α-KG) uptake carrier is increased as compared with a non-modified bacterium, and wherein the L-amino acid is an L-amino acid of glutamate family.

It is an aspect of the present invention to provide the method as described above, wherein the α-KG uptake carrier is a protein encoded by kgtP gene.

It is an aspect of the present invention to provide the method as described above, wherein the α-KG uptake carrier is a protein selected from the group consisting of:

(a) a protein comprising the amino acid sequence of SEQ ID NO: 8;

(b) a protein comprising the amino acid sequence of SEQ ID NO: 8, but which includes substitution, deletion, insertion, and/or addition of 1 to 10 amino acid residues, and wherein said protein has α-KG uptake activity; and (c) a protein comprising an amino acid sequence having an identity of 90% or higher to the amino acid sequence of SEQ ID NO: 8, and wherein said protein has α-KG uptake activity.

It is an aspect of the present invention to provide the method as described above, wherein the activity of the α-KG uptake carrier is increased by increasing the expression of a gene encoding the α-KG uptake carrier.

It is an aspect of the present invention to provide the method as described above, wherein the expression of the gene is increased by increasing the copy number of the gene and/or modifying an expression control sequence of the gene.

It is an aspect of the present invention to provide the method as described above, wherein the bacterium has further been modified so that the activity of phosphoketolase is increased as compared with a non-modified bacterium.

It is an aspect of the present invention to provide the method as described above, wherein the phosphoketolase comprises D-xylulose-5-phosphate phosphoketolase and/or fructose-6-phosphate phosphoketolase.

It is an aspect of the present invention to provide the method as described above, wherein the activity of the phosphoketolase is increased by increasing the expression of a gene encoding the phosphoketolase.

It is an aspect of the present invention to provide the method as described above, wherein the bacterium has further been modified so that the activity of α-ketoglutarate dehydrogenase and/or succinate dehydrogenase is reduced as compared with a non-modified bacterium.

It is an aspect of the present invention to provide the method as described above, wherein the bacterium is a *Corynebacterium* bacterium.

It is an aspect of the present invention to provide the method as described above, wherein the bacterium is *Corynebacterium glutamicum*.

It is an aspect of the present invention to provide the method as described above, wherein the L-amino acid of glutamate family is selected from the group consisting of L-glutamic acid, L-glutamine, L-proline, L-arginine, L-citrulline, L-ornithine, and combinations thereof.

It is an aspect of the present invention to provide the method as described above, wherein the L-amino acid of glutamate family is L-glutamic acid.

It is an aspect of the present invention to provide the method as described above, wherein the L-glutamic acid is monoammonium L-glutamate or monosodium L-glutamate.

It is an aspect of the present invention to provide the method as described above, wherein the bacterium has been further modified so as to harbor a mutant yggB gene.

It is an aspect of the present invention to provide the method as described above, wherein the mutant yggB gene is a yggB gene having a mutation that improves the L-glutamic acid-producing ability of the coryneform bacterium.

It is an aspect of the present invention to provide the method as described above, wherein the mutant yggB gene is a yggB gene having a mutation selected from the group consisting of:

(1) a mutation in the region coding for the amino acid residues at positions 419 to 533 of a wild-type YggB protein, (2) a mutation in the region coding for a transmembrane region of a wild-type YggB protein, and (3) a combination thereof.

It is an aspect of the present invention to provide the method as described above, wherein the wild-type YggB protein is a protein selected from the group consisting of:

(a) a protein comprising the amino acid sequence of SEQ ID NO: 12;

(b) a protein comprising the amino acid sequence of SEQ ID NO: 12, but which includes substitution, deletion, insertion, and/or addition of 1 to 10 amino acid residues, and wherein said protein is overexpressed in the coryneform bacterium, which provides an improved L-glutamic acid-producing ability of the coryneform bacterium; and (c) a protein comprising an amino acid sequence showing an identity of 90% or higher to the amino acid sequence of SEQ ID NO: 12, and having a property that an increased expression thereof in the coryneform bacterium provides an improved L-glutamic acid-producing ability of the coryneform bacterium.

According to the present invention, an ability for producing an L-amino acid of glutamate family of a coryneform bacterium can be improved, and the L-amino acid of glutamate family can be efficiently produced.

DESCRIPTION OF THE PREFERRED EMBODIMENTS

The method of the present invention is a method for producing an L-amino acid, the method including the steps of culturing a coryneform bacterium having an L-amino acid-producing ability in a medium, and collecting the L-amino acid from the medium, wherein the bacterium has been modified so that the activity of an α-ketoglutaric acid (α-KG) uptake carrier is increased, and wherein the L-amino acid is an L-amino acid of glutamate family. The coryneform bacterium used for the method can also be referred to as "bacterium of the present invention".

<1> Bacterium of the Present Invention

The bacterium of the present invention is a coryneform bacterium having an L-amino acid-producing ability, which has been modified so that the activity of an α-KG uptake carrier is increased.

<1-1> Coryneform Bacterium Having L-amino Acid-producing Ability

The phrase "bacterium having an L-amino acid-producing ability" can refer to a bacterium having an ability to produce and accumulate an objective L-amino acid in a medium or cells of the bacterium to such a degree that the L-amino acid can be collected, when the bacterium is cultured in the medium. The bacterium having an L-amino acid-producing ability may be a bacterium that is able to accumulate an objective L-amino acid in a medium in an amount larger than that obtainable with a non-modified strain. The term "non-modified strain" can refer to a control strain that has not been modified so that the activity of an α-KG uptake carrier is increased. That is, examples of the non-modified strain include wild-type strains and parental strains, such as *Corynebacterium glutamicum* strains ATCC 13869 and ATCC 13032. The bacterium having an L-amino acid-producing ability may be a bacterium that is able to accumulate an objective L-amino acid in a medium in an amount of 0.5 g/L or more, or 1.0 g/L or more.

The L-amino acid to be produced is an L-amino acid of glutamate family. The term "L-amino acid of glutamate family" collectively refers to L-glutamic acid and L-amino acids that are biosynthesized via L-glutamic acid as an intermediate. Examples of the L-amino acids that are biosynthesized via L-glutamic acid as an intermediate include L-glutamine, L-proline, L-arginine, L-citrulline, and L-ornithine. The bacterium may have an ability to produce only one kind of L-amino acid, or may have an ability to produce two or more kinds of L-amino acids.

The term "amino acid" can refer to an L-amino acid, unless otherwise stated. The term "L-amino acid" can refer to an L-amino acid in a free form, a salt thereof, or a mixture thereof, unless otherwise stated. Examples of salts will be described herein.

Examples of the coryneform bacterium include bacteria belonging to the genus *Corynebacterium, Brevibacterium, Microbacterium*, or the like.

Specific examples of the coryneform bacteria include the following species:

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes (Corynebacterium efficiens)*
*Corynebacterium herculis*
*Brevibacterium divaricatum (Corynebacterium glutamicum)*
*Brevibacterium flavum (Corynebacterium glutamicum)*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Corynebacterium ammoniagenes (Corynebacterium stationis)*
*Brevibacterium album*
*Brevibacterium cerinum*
*Microbacterium ammoniaphilum*

Specific examples of the coryneform bacteria include the following strains:

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens (Corynebacterium thermoaminogenes)* AJ12340 (FERM BP-1539)
*Corynebacterium herculis* ATCC 13868
*Corynebacterium glutamicum (Brevibacterium divaricatum)* ATCC 14020
*Corynebacterium glutamicum (Brevibacterium flavum)* ATCC 13826, ATCC 14067, AJ12418 (FERM BP-2205)
*Brevibacterium immariophilum* ATCC 14068
*Corynebacterium glutamicum (Brevibacterium lactofermentum)* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes (Corynebacterium stationis)* ATCC 6871, ATCC 6872

*Brevibacterium album* ATCC 15111
*Brevibacterium cerinum* ATCC 15112
*Microbacterium ammoniaphilum* ATCC 15354

The *Corynebacterium* bacteria include bacteria which have previously been classified into the genus *Brevibacterium*, but are presently united into the genus *Corynebacterium* (Int. J. Syst. Bacteriol., 41, 255 (1991)). Moreover, *Corynebacterium stationis* includes such a bacterium that has previously been classified into *Corynebacterium ammoniagenes*, but is presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are assigned to the respective strains, and the strains can be ordered by using these registration numbers (refer to atcc.org). The registration numbers of the strains are listed in the catalogue of the American Type Culture Collection. These strains can also be obtained from, for example, the depositories where the strains were deposited.

The bacterium may be a bacterium inherently having an L-amino acid-producing ability, or may be a bacterium modified so that it has an L-amino acid-producing ability. The bacterium having an L-amino acid-producing ability can be obtained by imparting an L-amino acid-producing ability to such a bacterium as mentioned above, or by enhancing an L-amino acid-producing ability of such a bacterium as mentioned above.

To impart or enhance an L-amino acid-producing ability, methods conventionally employed in the breeding of amino acid-producing strains of coryneform bacteria, *Escherichia* bacteria, and so forth (see "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. The activity of one L-amino acid biosynthetic enzyme may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a known mutagenesis treatment, and then selecting a strain exhibiting autotrophy, analogue resistance, or a metabolic regulation mutation, and having an L-amino acid-producing ability from the obtained mutant strains. Examples of the mutagenesis treatments include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. The activity of an enzyme can be enhanced by, for example, modifying a bacterium so that the expression of a gene encoding the enzyme is enhanced. Methods for enhancing gene expression are described in WO00/18935, EP 1010755 A, and so forth. The detailed procedures for enhancing enzyme activity will be described herein.

Furthermore, an L-amino acid-producing ability can also be imparted or enhanced by reducing the activity of an enzyme that catalyzes a reaction that branches away from the biosynthetic pathway of an objective L-amino acid to generate a compound other than the objective L-amino acid. The term "enzyme that catalyzes a reaction that branches away from the biosynthetic pathway of an objective L-amino acid to generate a compound other than the objective L-amino acid" referred to herein also includes enzymes involved in decomposition of the objective amino acid. The method for reducing the activity of an enzyme will be described later.

Hereafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-producing Bacteria>

Examples of methods for imparting or enhancing L-glutamic acid-producing ability include, for example, a method of modifying a bacterium so that the bacterium has an increased activity or activities of one or more kinds of enzymes selected from the L-glutamic acid biosynthesis enzymes. Examples of such enzymes include, but not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (gltA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are examples of the names of the genes encoding the enzymes (the same shall apply to the same occasions hereafter). It is preferable to enhance the activity or activities of one or more kinds of enzymes selected from, for example, glutamate dehydrogenase, citrate synthase, phosphoenol pyruvate carboxylase, and methylcitrate synthase, among these enzymes.

Examples of coryneform bacteria modified so that the expression of the glutamate synthetase gene (gltBD) is increased include those disclosed in WO99/07853.

Examples of methods for imparting or enhancing L-glutamic acid-producing ability also include, for example, a method of modifying a bacterium so that the bacterium has a reduced activity or activities of one or more kinds of enzymes selected from the enzymes that catalyze a reaction branching away from the biosynthesis pathway of L-glutamine to generate a compound other than L-glutamic acid. Examples of such enzymes include, but not particularly limited to, isocitrate lyase (aceA), α-ketoglutarate dehydrogenase (sucA, odhA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). It is preferable to reduce or delete, for example, the α-ketoglutarate dehydrogenase activity, among these enzymes.

Coryneform bacteria in which the α-ketoglutarate dehydrogenase activity is reduced or eliminated, and methods for obtaining those are disclosed in WO2008/075483. Specific examples of coryneform bacteria in which the α-ketoglutarate dehydrogenase activity is reduced or eliminated include, for example, the following strains.

*Corynebacterium glutamicum (Brevibacterium lactofermentum)* L30-2 strain (Japanese Patent Laid-open (Kokai) No. 2006-340603)

*Corynebacterium glutamicum (Brevibacterium lactofermentum)* ΔS strain (WO95/34672)

*Corynebacterium glutamicum (Brevibacterium lactofermentum)* AJ12821 (FERM BP-4172, French Patent No. 9401748)

*Corynebacterium glutamicum (Brevibacterium flavum)* AJ12822 (FERM BP-4173, French Patent No. 9401748)

*Corynebacterium glutamicum* AJ12823 (FERM BP-4174, French Patent No. 9401748)

*Corynebacterium glutamicum* L30-2 strain (Japanese Patent Laid-open (Kokai) No. 2006-340603)

Examples of L-glutamic acid-producing bacteria and parent strains that can be used to derive them also include strains in which both the α-ketoglutarate dehydrogenase (sucA) activity and the succinate dehydrogenase (sdh) activity are reduced or eliminated (Japanese Patent Laid-open (Kokai) No. 2010-041920). Specific examples of such strains include, for example, *Corynebacterium glutamicum* 8L3GΔSDH strain, which is the odhAsdhA double-deficient strain of *Corynebacterium glutamicum* ATCC 14067 (Japanese Patent Laid-open (Kokai) No. 2010-041920).

Examples of methods for imparting or enhancing L-glutamine-producing ability also include, for example, a method of enhancing the expression of yhfK gene (WO2005/085419) or ybjL gene (WO2008/133161), which is an L-glutamic acid secretion gene.

Furthermore, examples of methods for imparting or enhancing L-glutamic acid-producing ability to or in coryneform bacteria also include methods of imparting resistance to an organic acid analogue, respiratory inhibitor, or the like, and methods of imparting sensitivity to a cell wall synthesis inhibitor. Specific examples of such methods include, for example, the method of imparting monofluoroacetic acid resistance (Japanese Patent Laid-open (Kokai) No. 50-113209), the method of imparting adenine resistance or thymine resistance (Japanese Patent Laid-open (Kokai) No. 57-065198), the method of attenuating urease (Japanese Patent Laid-open (Kokai) No. 52-038088), the method of imparting malonic acid resistance (Japanese Patent Laid-open (Kokai) No. 52-038088), the method of imparting resistance to benzopyrones or naphthoquinones (Japanese Patent Laid-open (Kokai) No. 56-1889), the method of imparting HOQNO resistance (Japanese Patent Laid-open (Kokai) No. 56-140895), the method of imparting α-ketomalonic acid resistance (Japanese Patent Laid-open (Kokai) No. 57-2689), the method of imparting guanidine resistance (Japanese Patent Laid-open (Kokai) No. 56-35981), the method of imparting sensitivity to penicillin (Japanese Patent Laid-open (Kokai) No. 4-88994), and so forth.

Specific examples of such resistant or sensitive bacteria include the following strains.

*Corynebacterium glutamicum (Brevibacterium flavum)* AJ3949 (FERM BP-2632, refer to Japanese Patent Laid-open (Kokai) No. 50-113209)

*Corynebacterium glutamicum* AJ11628 (FERM P-5736, refer to Japanese Patent Laid-open (Kokai) No. 57-065198)

*Corynebacterium glutamicum (Brevibacterium flavum)* AJ11355 (FERM P-5007, refer to Japanese Patent Laid-open (Kokai) No. 56-1889)

*Corynebacterium glutamicum* AJ11368 (FERM P-5020, refer to Japanese Patent Laid-open (Kokai) No. 56-1889)

*Corynebacterium glutamicum (Brevibacterium flavum)* AJ11217 (FERM P-4318, refer to Japanese Patent Laid-open (Kokai) No. 57-2869)

*Corynebacterium glutamicum* AJ11218 (FERM P-4319, refer to Japanese Patent Laid-open (Kokai) No. 57-2869)

*Corynebacterium glutamicum (Brevibacterium flavum)* AJ11564 (FERM BP-5472, refer to Japanese Patent Laid-open (Kokai) No. 56-140895)

*Corynebacterium glutamicum (Brevibacterium flavum)* AJ11439 (FERM BP-5136, refer to Japanese Patent Laid-open (Kokai) No. 56-35981)

*Corynebacterium glutamicum* H7684 (FERM BP-3004, refer to Japanese Patent Laid-open (Kokai) No. 04-88994)

*Corynebacterium glutamicum (Brevibacterium lactofermentum)* AJ11426 (FERM P-5123, refer to Japanese Patent Laid-open (Kokai) No. 56-048890)

*Corynebacterium glutamicum* AJ11440 (FERM P-5137, refer to Japanese Patent Laid-open (Kokai) No. 56-048890)

*Corynebacterium glutamicum (Brevibacterium lactofermentum)* AJ11796 (FERM P-6402, refer to Japanese Patent Laid-open (Kokai) No. 58-158192)

Furthermore, examples of methods for imparting or enhancing L-glutamic acid-producing ability to or in coryneform bacteria also include a method of enhancing the expression of yggB gene and a method of introducing a mutant yggB gene having a mutation in the coding region (WO2006/070944). That is, the bacterium may have been modified so that the expression of yggB gene is increased, or may have been modified so as to harbor (have) a mutant yggB gene.

The yggB gene is a gene encoding a mechanosensitive channel. Examples of the yggB gene include yggB genes of coryneform bacteria. Specific examples of the yggB genes of coryneform bacteria include, for example, yggB genes of *Corynebacterium glutamicum* ATCC 13869, *Corynebacterium glutamicum* ATCC13032, *Corynebacterium glutamicum* ATCC 14967, and *Corynebacterium melassecola* ATCC17965 (WO2006/070944). The yggB gene of *Corynebacterium glutamicum* ATCC 13032 corresponds to the sequence complementary to the sequence of the nucleotide numbers 1,336,091 to 1,337,692 in the genome sequence registered as Genbank Accession No. NC_003450 in the NCBI database, and is also called NCgl1221. The YggB protein encoded by the yggB gene of *Corynebacterium glutamicum* ATCC 13032 is registered as GenBank accession No. NP_600492. In addition, the nucleotide sequence of the yggB gene of *Corynebacterium glutamicum* 2256 (ATCC 13869) and the amino acid sequence of the YggB protein encoded by the gene are shown in SEQ ID NOS: 11 and 12, respectively.

In the present invention, a yggB gene having the "specific mutation" described later can also be referred to as "mutant yggB gene", and a protein encoded thereby is also referred to as "mutant YggB protein". Furthermore, a yggB gene not having the "specific mutation" described herein can also be referred to as a "wild-type yggB gene", and a protein encoded thereby can also be referred to as a "wild-type YggB protein". In addition, as for the YggB protein, change of the amino acid sequence caused by the "specific mutation" in the yggB gene is also referred to as "specific mutation". The term "wild-type" referred to herein is used for convenience to distinguish the "wild-type" yggB gene or YggB protein from the "mutant" yggB gene or YggB protein, and the "wild-type" yggB gene or YggB protein is not limited to those obtained as natural substances, so long as it does not have the "specific mutation". Examples of the wild-type YggB protein include the YggB proteins exemplified above, such as YggB protein having the amino acid sequence of SEQ ID NO: 12. Examples of the wild-type YggB protein also include conservative variants (variants in which the original function thereof is maintained) of the YggB proteins exemplified above, provided that the conservative variants do not have the "specific mutation". The "original function" regarding the YggB protein may be, for example, a function as a mechanosensitive channel or a property that an increased expression thereof in a coryneform bacterium provides an improved L-glutamic acid-producing ability of the coryneform bacterium.

The "specific mutation" is not particularly limited, so long as it changes the amino acid sequence of the YggB protein such as those described above to thereby improve an L-glutamic acid-producing ability of a coryneform bacterium. Examples of the "specific mutation" include mutation on the C-terminus side and mutation in a transmembrane region. The "specific mutation" may also be a combination of these.

(1) Mutation on C-terminus Side

The mutation on the C-terminus side is a mutation introduced into the region of the wild-type yggB gene coding for the amino acid residues of the positions 419 to 533 of the wild-type YggB protein. The mutation on the C-terminus side may be introduced at one or more sites in the region. The type of change of the amino acid sequence induced by the mutation on the C-terminus side is not particularly limited. The mutation on the C-terminus side may be a mutation causing amino acid substitution (missense mutation), insertion of amino acid residue, deletion of amino acid residue, introduction of stop codon (nonsense mutation), frame shift mutation, or a combination of these. The mutation on the C-terminus side can be, for example, a mutation for inserting a nucleotide sequence such as an insertion sequence (henceforth also referred to as "IS") or transposon.

Insertion of Nucleotide Sequence

Examples of the mutation on the C-terminus side can include, for example, a mutation that inserts a nucleotide sequence at the site coding for the valine residue at the position 419 of the wild-type YggB protein (2A-1 type mutation). The 2A-1 type mutation may be, for example, a mutation that causes deletion or substitution for a part or all of the amino acid residues at the positions 419 to 533 of the wild-type YggB protein. Specific examples of the mutant yggB gene having the 2A-1 type mutation can include, for example, the yggB gene including IS inserted into the next of "G" at the position 1255 in SEQ ID NO: 11, and thereby coding for a mutant YggB protein having a full length of 423 amino residues, which is shorter than that of the original wild-type YggB protein (SEQ ID NO: 12). The nucleotide sequence of this mutant yggB gene (V419::IS) and the amino acid sequence of the mutant YggB protein encoded by the gene are shown in SEQ ID NOS: 13 and 14, respectively. In the SEQ ID NO: 13, the positions 1 to 1269 correspond to CDS for this mutant YggB protein (V419::IS).

Substitution for Proline Residues

Examples of the mutation on the C-terminus side can also include, for example, a mutation that replaces a proline residue present at the positions 419 to 533 of the wild-type YggB protein with another amino acid residue. Examples of such a proline residue can include the proline residues at the positions 424, 437, 453, 457, 462, 469, 484, 489, 497, 515, 529, and 533 of the wild-type YggB protein. It is a particular example to replace the proline residue(s) of the position(s) 424 and/or 437 with other amino acid residue(s). The "other amino acid" is not particularly limited so long as it is a naturally occurring amino acid other than proline. Examples of the "other amino acid" can include Lys, Glu, Thr, Val, Leu, Ile, Ser, Asp, Asn, Gln, Arg, Cys, Met, Phe, Trp, Tyr, Gly, Ala, and His. For example, the proline residue at the position 424 may be replaced with a hydrophobic amino acid (Ala, Gly, Val, Leu, or Ile), or a branched chain amino acid (Leu, Val, or Ile). Furthermore, for example, the proline residue at the position 437 may be replaced with a residue of an amino acid having hydroxyl group in the side chain (Thr, Ser, or Tyr), or with a Ser residue.

(2) Mutation in Transmembrane Region

The YggB protein is estimated to have five transmembrane regions. The transmembrane regions correspond to the amino acid residues of the positions 1 to 23 (first transmembrane region), the positions 25 to 47 (second transmembrane region), the positions 62 to 84 (third transmembrane region), the positions 86 to 108 (fourth transmembrane region), and the positions 110 to 132 (fifth transmembrane region) of the wild-type YggB protein. The mutation in a transmembrane region is a mutation in the regions coding for these transmembrane regions of the wild-type yggB gene. The mutation in transmembrane region may be introduced into one or more sites in the regions. The mutation in transmembrane region can be a mutation that induces substitution, deletion, addition, insertion, or inversion of one or several amino acid residues, but does not include any frame shift mutation or nonsense mutation. The number meant by the phrase "one or several" can be 1 to 20, 1 to 10, 1 to 5, or 1 to 3. Examples of the mutation in a transmembrane region include a mutation that inserts one or several amino acid residues, such as Cys-Ser-Leu, between the leucine residue at the position 14 and the tryptophan residue at the position 15; a mutation that replaces the alanine residue at the position 100 with another amino acid residue, such as a residue of an amino acid having hydroxyl group in the side chain (i.e. Thr, Ser, or Tyr), Thr is a particular example; a mutation that replaces the alanine residue at the position 111 with another amino acid residue such as a residue of an amino acid having hydroxyl group in the side chain (i.e. Thr, Ser, or Tyr), Thr is a particular example; in the wild-type YggB protein.

An "amino acid residue at the position X of the wild-type YggB protein" means the amino acid residue corresponding to that of the position X in SEQ ID NO: 12, unless otherwise stated. The "position X" in an amino acid sequence is counted from the N-terminus of the amino acid sequence, and the amino acid residue of the N-terminus is the amino acid residue of the position 1. That is, the aforementioned positions of amino acid residues indicate relative positions, and the absolute positions thereof may shift due to deletion, insertion, addition, or the like of an amino acid residue or residues. For example, the "amino acid residue at the position 419 of the wild-type YggB protein" means the amino acid residue corresponding to that of the position 419 in SEQ ID NO: 12, and when one amino acid residue is deleted at a position on the N-terminus side of the position 419, the 418th amino acid residue from the N-terminus is "the amino acid residue at the position 419 of the wild-type YggB protein". Furthermore, when one amino acid residue is inserted a position on the N-terminus side of the position 419, the 420th amino acid residue from the N-terminus is "the amino acid residue at the position 419 of the wild-type YggB protein". Specifically, for example, amino acid residues of the positions 419 to 529 of the YggB protein of Corynebacterium glutamicum ATCC 14967 correspond to amino acid residues of the positions 419 to 533 of the wild-type YggB protein.

To determine the amino acid residue that is "the amino acid residue corresponding to that of the position X in SEQ ID NO: 12" in the amino acid sequence of an arbitrary YggB protein, alignment between the amino acid sequence of the arbitrary YggB protein and the amino acid sequence of SEQ ID NO: 12 can be performed. The alignment can be performed by, for example, using known gene analysis software. Specific examples of such software include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant yggB gene can be obtained by modifying a wild-type yggB gene so as to have the aforementioned "specific mutation". The modification of DNA can be performed by a known method. For example, an objective mutation can be introduced into an objective site of DNA by the site-specific mutation method. Specific examples of the site-specific mutation method include, for example, a method of using PCR (Higuchi, R., 61, in PCR Technology, Erlich, H. A. Eds., Stockton Press, 1989; Carter P., Meth. In Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Furthermore, a mutant yggB gene can also be obtained by chemical synthesis.

Such modification of a bacterium that the bacterium has a mutant yggB gene can be attained by introducing the mutant yggB gene into the bacterium. Such modification of a bacterium that the bacterium has a mutant yggB gene can also be attained by introducing a mutation into the yggB gene of the bacterium through natural mutation or a treatment with a mutagen.

<L-Glutamine-producing Bacteria>

Examples of the method for imparting or enhancing L-glutamine-producing ability include, for example, a method of modifying a bacterium so that the activity or activities of one or more L-glutamine biosynthesis enzymes are enhanced. Examples of such enzymes include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP 1229121).

Examples of the method for imparting or enhancing L-glutamine-producing ability also include, for example, a method of modifying a bacterium so that the activity or activities of one or more kinds of enzymes that catalyze a reaction branching away from the biosynthesis pathway of L-glutamine to generate a compound other than L-glutamine are reduced. Examples of such enzymes include, but not particularly limited to, glutaminase.

Specific examples of L-glutamine-producing bacteria and parent strains that can be used to derive them include, for example, coryneform bacteria in which the activity or activities of glutamate dehydrogenase (gdhA) and/or glutamine synthetase (glnA) (EP 1229121, EP 1424398) are enhanced, and coryneform bacteria in which the glutaminase activity (Japanese Patent Laid-open (Kokai) No. 2004-187684) is reduced.

Examples of the methods for imparting or enhancing L-glutamine-producing ability to or in coryneform bacteria also include the method of imparting 6-diazo-5-oxo-norleucine resistance (Japanese Patent Laid-open (Kokai) No. 3-232497), the method of imparting purine analogue resistance and methionine sulfoxide resistance (Japanese Patent Laid-open (Kokai) No. 61-202694), and the method of imparting α-ketomalonic acid resistance (Japanese Patent Laid-open (Kokai) No. 56-151495). Specific examples of coryneform bacteria having L-glutamine-producing ability include, for example, the following strains.

Corynebacterium glutamicum (Brevibacterium flavum) AJ11573 (FERM P-5492, Japanese Patent Laid-open (Kokai) No. 56-151495)

Corynebacterium glutamicum (Brevibacterium flavum) AJ11576 (FERM BP-10381, Japanese Patent Laid-open (Kokai) No. 56-151495)

Corynebacterium glutamicum (Brevibacterium flavum) AJ12212 (FERM P-8123, Japanese Patent Laid-open (Kokai) No. 61-202694)

<L-Proline-producing Bacteria>

Examples of methods for imparting or enhancing L-proline-producing ability include, for example, a method of modifying a bacterium so that the bacterium has an increased activity or activities of one or more kinds of L-proline biosynthesis enzymes. Examples of such enzymes include glutamate-5-kinase (proB), γ-glutamylphosphate reductase, and pyroline-5-carboxylate reductase (putA). For enhancing the activity of such an enzyme, for example, the proB gene encoding a glutamate kinase desensitized to feedback inhibition by L-proline (German Patent No. 3127361) can be used.

Examples of methods for imparting or enhancing L-glutamine-producing ability also include, for example, a method of modifying a bacterium so that the bacterium has a reduced activity of an enzyme involved in decomposition of L-proline. Examples of such an enzyme include proline dehydrogenase and ornithine aminotransferase.

<L-Arginine-producing Bacteria>

Examples of methods for imparting or enhancing L-arginine-producing ability include, for example, a method of modifying a bacterium so that the bacterium has an increased activity or activities of one or more kinds of L-arginine biosynthesis enzymes. Examples of such enzymes include, but not particularly limited to, N-acetylglutamate synthase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinate synthetase (argG), argininosuccinate lyase (argH), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (European Patent Laid-open No. 1170361) can preferably be used.

Examples of L-arginine-producing bacteria and parent strains that can be used to derive them also include such coryneform bacteria as a strain deficient in ArgR, which is an arginine repressor (U.S. Published Patent Application No.

20020045223), and a strain in which glutamine synthetase activity is increased (U.S. Published Patent Application No. 20050014236).

Examples of L-arginine-producing bacteria and parent strains that can be used to derive them also include mutant strains of coryneform bacteria, the mutant strains having resistance to an amino acid analogue or the like. Examples of such strains include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability include the following strains.

Corynebacterium glutamicum (Brevibacterium flavum) AJ11169 (FERM BP-6892)

Corynebacterium glutamicum (Brevibacterium lactofermentum) AJ12092 (FERM BP-6906)

Corynebacterium glutamicum (Brevibacterium flavum) AJ11336 (FERM BP-6893)

Corynebacterium glutamicum (Brevibacterium flavum) AJ11345 (FERM BP-6894)

Corynebacterium glutamicum (Brevibacterium lactofermentum) AJ12430 (FERM BP-2228)

<L-Citrulline-producing Bacteria and L-ornithine-producing Bacteria>

The biosynthetic pathways of L-citrulline and L-ornithine are common to that of L-arginine. Therefore, an ability to produce L-citrulline and/or L-ornithine can be imparted or enhanced by increasing the activity or activities of N-acetylglutamate synthase (argA), N-acetylglutamyl phosphate reductase (argC), ornithine acetyltransferase (argJ), N-acetylglutamate kinase (argB), acetylornithine transaminase (argD), and/or acetylornithine deacetylase (argE) (WO2006/35831).

The methods for imparting or enhancing L-glutamic acid-producing ability may also be effective for imparting or enhancing an ability to produce these L-amino acids that are biosynthesized via L-glutamic acid as an intermediate, such as L-glutamine, L-proline, L-arginine, L-citrulline, and L-ornithine. Hence, a bacterium having an ability to produce any of these L-amino acids that are biosynthesized via L-glutamic acid as an intermediate may have such a property possessed by an L-glutamic acid-producing bacterium as described above, as required. For example, a bacterium having an ability to produce any of these L-amino acids that are biosynthesized via L-glutamic acid as an intermediate may have been modified so that the activity of α-ketoglutarate dehydrogenase and/or succinate dehydrogenase is reduced.

Examples of methods for imparting or enhancing L-amino acid-producing ability such as L-glutamic acid-producing ability also include a method of modifying a bacterium so that the activity of phosphoketolase is increased (WO2006/016705). Hence, the bacterium may be modified so that the activity of phosphoketolase is increased. Examples of phosphoketolase include D-xylulose-5-phosphate phosphoketolase and fructose-6-phosphate phosphoketolase. Either one of the D-xylulose-5-phosphate phosphoketolase activity and the fructose-6-phosphate phosphoketolase activity may be enhanced, or both may be enhanced.

The term "D-xylulose-5-phosphate phosphoketolase activity" can refer to an activity for converting xylulose-5-phosphate into glycelaldehyde-3-phosphate and acetyl phosphate with consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183:2929-2936, 2001). Examples of D-xylulose-5-phosphate phosphoketolase include those of bacteria belonging to the genera *Acetobacter, Bifidobacterium, Lactobacillus, Thiobacillus, Streptococcus, Methylococcus, Butyrivibrio*, and *Fibrobacter*, and yeast belonging to the genera *Candida, Rhodotorula, Rhodosporidium, Pichia, Yarrowia, Hansenula, Kluyveromyces, Saccharomyces, Trichosporon*, and *Wingea*. Specific examples of D-xylulose-5-phosphate phosphoketolase and genes encoding them are disclosed in WO2006/016705.

The term "fructose-6-phosphate phosphoketolase activity" can refer to an activity for converting fructose-6-phosphate into erythrose-4-phosphate and acetyl phosphate with consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001). Examples of fructose-6-phosphate phosphoketolase include those of bacteria belonging to the genera *Acetobacter, Bifidobacterium, Chlorobium, Brucella, Methylococcus*, and *Gardnerella*, and yeast belonging to the genera *Rhodotorula, Candida*, and *Saccharomyces*. Specific examples of fructose-6-phosphate phosphoketolase and genes encoding them are disclosed in WO2006/016705.

Both the D-xylulose-5-phosphate phosphoketolase activity and the fructose-6-phosphate phosphoketolase activity may also be retained by a single enzyme (i.e. D-xylulose-5-phosphate phosphoketolase/fructose-6-phosphate phosphoketolase).

The nucleotide sequence of phosphoketolase gene (xfp gene) of *Bifidobacterium longum* JCM1217 and the amino acid sequence of phosphoketolase (Xfp protein) encoded by the gene are shown in SEQ ID NOS: 9 and 10, respectively.

Furthermore, examples of methods for imparting or enhancing an L-amino acid-producing ability can also include, for example, a method of modifying a bacterium so that the activity or activities of one or more of proteins involved in the glycometabolism and proteins involved in the energy metabolism are increased.

Examples of the proteins involved in the glycometabolism include proteins involved in uptake of saccharides and the glycolysis system enzymes. Examples of genes encoding the proteins involved in the glycometabolism include the glucose-6-phosphate isomerase gene (pgi, WO01/02542), pyruvate carboxylase gene (pyc, WO99/18228, EP 1092776 A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP 1149911 A), and sucrose utilization gene (scrAB operon, U.S. Pat. No. 7,179,623).

Examples of genes encoding the proteins involved in the energy metabolism include the transhydrogenase gene (pntAB, U.S. Pat. No. 5,830,716) and cytochrome bo-type oxidase gene (cyoB, EP 1070376 A).

The genes and proteins used for breeding L-amino acid-producing bacteria may have, for example, the nucleotide sequences and amino acid sequences of known genes and proteins, such as those exemplified above, respectively.

Also, the genes and proteins used for breeding L-amino acid-producing bacteria may be conservative variants of known genes and proteins, such as those exemplified above, respectively. Specifically, for example, the genes used for breeding L-amino acid-producing bacteria may each be a gene encoding a protein having an amino acid sequence of a known protein, but including substitution, deletion, insertion, and/or addition of one or several amino acid residues at one or several positions, so long as the original function thereof is maintained. For the conservative variants of genes and proteins, the descriptions for conservative variants of the α-KG uptake carrier gene and α-KG uptake carrier mentioned later can be applied, mutatis mutandis.

<1-2> Enhancement of α-KG Uptake Carrier Activity

The bacterium is modified so that the activity of an α-KG uptake carrier (α-KG uptake carrier activity) is increased. Specifically, the bacterium is modified so that the activity of an α-KG uptake carrier (α-KG uptake carrier activity) is increased as compared with a non-modified strain. The bacterium can be obtained by modifying a coryneform bacterium having an L-amino acid-producing ability so that the activity of an α-KG uptake carrier is increased. The bacterium can also be obtained by modifying a coryneform bacterium so that the activity of an α-KG uptake carrier is increased, and then imparting or enhancing an L-amino acid-producing ability. The bacterium may also be a bacterium that has acquired an L-amino acid-producing ability by being modified so that the activity of an α-KG uptake carrier is increased. The bacterium may have such a property possessed by an L-amino acid-producing bacterium as described above, as required. For example, the bacterium may have been modified so that the activity of phosphoketolase is increased. The modifications for constructing the bacterium can be performed in an arbitrary order.

By modifying a coryneform bacterium so that the activity of an α-KG uptake carrier is increased, an L-amino acid-producing ability of the coryneform bacterium can be improved, and that is, the production of an L-amino acid by using the coryneform bacterium can be increased. In particular, by modifying a coryneform bacterium so that the activity of an α-KG uptake carrier is increased, an L-amino acid-producing ability of the coryneform bacterium under conditions where α-KG is produced as a byproduct can be improved.

Hereafter, α-KG uptake carriers and genes encoding them will be explained.

The term "α-KG uptake carrier" can refer to a protein having α-KG uptake activity. The phrase "α-KG uptake activity" can refer to an activity for taking up α-KG into the inside of a cell from the outside of the cell. A gene encoding an α-KG uptake carrier can also be referred to as "α-KG uptake carrier gene".

Examples of the α-KG uptake carrier include KgtP protein, which is encoded by kgtP gene. Examples of kgtP gene include those of *Escherichia coli*, *Pantoea ananatis*, *Salmonella enterica*, *Shigella flexneri*, *Shigella dysenteriae*, *Burkholderia pseudomallei*, *Bradyrhizobium diazoefficiens*, *Campylobacter jejuni*, and *Ralstonia solanacearum*. The nucleotide sequences of the kgtP genes derived from these various organisms and the amino acid sequences of the KgtP proteins encoded by these genes can be easily obtained from public databases such as NCBI. The kgtP gene of *Escherichia coli* K-12 MG1655 corresponds to the sequence complementary to the sequence at positions 2724448 to 2725746 in the genome sequence registered at the NCBI database as GenBank accession NC_000913 (VERSION NC_000913.3 GI:556503834). Further, the KgtP protein of *Escherichia coli* K-12 MG1655 is registered as GenBank accession NP_417082 (version NP_417082.1 GI:16130512). The nucleotide sequence of the kgtP gene of the strain MG1655 and the amino acid sequence of the KgtP protein encoded by the gene are shown in SEQ ID NOS: 7 and 8, respectively. That is, the α-KG uptake carrier gene may be, for example, a gene having the nucleotide sequence of any of the kgtP genes exemplified above, such as the nucleotide sequence shown as SEQ ID NO: 7. Also, the α-KG uptake carrier may be, for example, a protein having the amino acid sequence of any of the KgtP proteins exemplified above, such as the amino acid sequence shown as SEQ ID NO: 8. The expression "a gene or protein has a nucleotide or amino acid sequence" encompasses when a gene or protein includes the nucleotide or amino acid sequence among other sequences, and also when a gene or protein consists of only the nucleotide or amino acid sequence.

The α-KG uptake carrier gene may be a variant of any of the α-KG uptake carrier genes exemplified above (e.g. kgtP genes exemplified above), so long as the original function thereof is maintained. Similarly, the α-KG uptake carrier may be a variant of any of the α-KG uptake carriers exemplified above (e.g. KgtP proteins exemplified above), so long as the original function thereof is maintained. Such a variant that maintains the original function thereof is also referred to as "conservative variant". The term "kgtP gene" includes not only the kgtP genes exemplified above, but also includes conservative variants thereof. Similarly, the term "KgtP protein" includes not only the KgtP proteins exemplified above, but also includes conservative variants thereof. Examples of the conservative variants include, for example, homologues and artificially modified versions of the α-KG uptake carrier genes and α-KG uptake carriers exemplified above.

The expression "the original function is maintained" means that a variant of gene or protein has a function (such as activity or property) corresponding to the function (such as activity or property) of the original gene or protein. The expression "the original function is maintained" used for a gene means that a variant of the gene encodes a protein that maintains the original function. That is, the expression "the original function is maintained" used for the α-KG uptake carrier gene means that a variant of the gene encodes a protein having α-KG uptake activity. The expression "the original function is maintained" used for the α-KG uptake carrier means that a variant of the protein has α-KG uptake activity.

The α-KG uptake activity of a protein can be measured by, for example, incubating cells expressing the protein with α-KG, and measuring the uptake of α-KG into the cells dependent on the protein (Seol W, Shatkin A J. *Escherichia coli* kgtP encodes an alpha-ketoglutarate transporter. Proc Natl Acad Sci USA. 1991 May 1; 88(9):3802-6.).

Hereafter, examples of the conservative variants will be explained.

Homologues of the α-KG uptake carrier genes or homologues of the α-KG uptake carriers can be easily obtained from public databases by, for example, BLAST search or FASTA search using any of the nucleotide sequences of the α-KG uptake carrier genes exemplified above or any of the amino acid sequences of the α-KG uptake carriers exemplified above as a query sequence. Further, homologues of the α-KG uptake carrier genes can be obtained by, for example, PCR using a chromosome of various organisms such as coryneform bacteria as the template, and oligonucleotides prepared on the basis of any of the nucleotide sequences of these known α-KG uptake carrier genes as primers.

The α-KG uptake carrier gene may be a gene encoding a protein having any of the aforementioned amino acid sequences (e.g. the amino acid sequence shown as SEQ ID NO: 8), but which includes substitution, deletion, insertion, and/or addition of one or several amino acid residues at one or several positions, so long as the original function is maintained. For example, the N-terminus and/or the C-terminus of the encoded protein may be elongated or shortened. Although the number meant by the term "one or several" mentioned above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues are each a conservative mutation that maintains the normal or native function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion, or the like of amino acid residues as mentioned above includes a naturally occurring mutation due to an individual difference, or a difference of species of the organism from which the gene is derived (mutant or variant).

The α-KG uptake carrier gene may be a gene encoding a protein having an amino acid sequence showing a homology of, for example, 50% or more, 65% or more, or 80% or more, 90% or more, 95% or more, 97% or more, or 99% or more, to the total amino acid sequence of any of the aforementioned amino acid sequences, so long as the original function is maintained. In this description, "homology" means "identity".

The α-KG uptake carrier gene may also be a gene, such as a DNA, that is able to hybridize under stringent conditions with a probe that can be prepared from any of the aforementioned nucleotide sequences (e.g. the nucleotide sequence shown as SEQ ID NO: 7), such as a sequence complementary to a partial or entire sequence of any of the aforementioned nucleotide sequences, so long as the original function is maintained. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 50%, 65%, or 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Further, since the degeneracy of codons differs depending on the host, arbitrary codons in the α-KG uptake carrier gene may be replaced with respective equivalent codons. That is, the α-KG uptake carrier gene may be a variant of any of the α-KG uptake carrier genes exemplified above due to the degeneracy of the genetic code. For example, the α-KG uptake carrier gene may be a gene modified so that it has optimal codons according to codon frequencies in a host to be used.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12.

In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

The aforementioned descriptions concerning conservative variants of the genes and proteins can be applied mutatis mutandis to variants of arbitrary proteins such as L-amino acid biosynthesis system enzymes and genes encoding them.

<1-3> Methods for Increasing Activity of Protein

Hereafter, the methods for increasing the activity of a protein such as the α-KG uptake carrier will be explained.

The expression "the activity of a protein is increased" can mean that the activity of the protein is increased as compared with a non-modified strain. Specifically, the expression "the activity of a protein is increased" may mean that the activity of the protein per cell is increased as compared with that of a non-modified strain. The term "non-modified strain" as used herein can refer to a strain that has not been modified so that the activity of an objective protein is increased, and hence can be used as a control. The non-modified strain can also be referred to as "non-modified bacterium". Examples of the non-modified strain include a wild-type strain and/or a parental strain. Specific examples of the non-modified strain can include non-modified versions of the chosen bacterial strains, or similar strains, and can particularly include the exact strain of the chosen coryneform bacterium. More specific examples of the non-modified strain include strains exemplified above, such as *C. glutamicum* ATCC 13032 and *C. glutamicum* ATCC 13869. That is, in an embodiment, the activity of a protein may be increased as compared with the exact strain of bacteria, or it may be increased as compared with a strain from the same species of bacteria, but not the exact strain. For example, if *C. glutamicum* ATCC 13869 is modified, the activity of a protein may be increased as compared with the exact strain ATCC 13869, or it may be increased as compared with a different strain of *C. glutamicum*, for example, *C. glutamicum* ATCC 13032.

The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the protein (i.e. the amount of the protein). Furthermore, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified bacterial strain. The activity of the protein may be increased to, for example, 1.5 times or more, 2 times or more, or 3 times or more of that of a non-modified strain. Further, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The phrase "the expression of a gene is increased" can mean that the expression the gene is increased as compared with a non-modified strain such as a wild-type strain or a parental strain. Specifically, the phrase "the expression of a gene is increased" may mean that the expression amount of the gene per cell is increased as compared with that of a non-modified strain. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" is also referred to as "the expression of a gene is enhanced". The expression of a gene may be increased to, for example, 1.5 times or more, 2 times or more, or 3 times or more of that of a non-modified strain. Furthermore, when "the expression of a gene is increased" can include not only when the expression amount of an objective gene is increased in a strain that inherently expresses the objective gene, but also when the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria include pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVK9 described in WO2007/046389; pVS7 described in WO2013/069634; and pVC7 described in Japanese Patent Laid-open (Kokai) No. 9-070291.

When a gene is introduced, it is sufficient that the gene is expressibly harbored by a host. Specifically, it is sufficient that the gene is harbored by a host so that it is expressed under the control of a promoter that functions in the host. The phrase "a promoter that functions in a host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in a host. The terminator may be a terminator derived from the host, or a heterogenous terminator. The terminator may be the native terminator of the gene to be introduced, or a terminator of another gene.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by a host. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced. The case of "introducing two or more genes" can include, for example, cases of introducing respective genes encoding two or more kinds of proteins (such as enzymes), introducing respective genes encoding two or more subunits constituting a single protein complex (such as enzyme complex), and a combination of the foregoing cases.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein include substitution, deletion, insertion, or addition of amino acid residues. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be entirely synthesized.

In addition, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that encode the subunits may be enhanced. It is usually preferable to enhance the expression of all of the plurality of genes encoding the subunits. Furthermore, the subunits constituting the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene. Examples of the expression control sequence include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" means a promoter providing an improved transcription of a gene compared with an inherently existing wild-type promoter of the gene. Examples of stronger promoters usable in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Further, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a synonymous codon more frequently used. That is, the gene to be introduced may be modified, for example, so as to contain optimal codons according to the frequencies of codons observed in a host to be used. Codons can be replaced by, for example, the site-specific mutation method for introducing an objective mutation into an objective site of DNA. Alternatively, a gene fragment in which objective codons are replaced may be totally synthesized. Frequencies of codons in various organisms are disclosed in the "Codon Usage Database" (kazusa.or.jp/codon; Nakamura, Y et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the enzyme. Enhancement of the specific activity also includes desensitization to feedback inhibition. That is, when a protein is subject to feedback inhibition by a metabolite, the activity of the protein can be increased by making a host harbor a gene encoding a mutant protein that has been desensitized to the feedback inhibition. In the present invention, "desensitization to feedback inhibition" includes attenuation and elimination of the feedback inhibition. A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, a site-specific mutation method such as that mentioned above. The mutation may also be introduced by, for example, a mutagenesis treatment. Examples of the mutagenesis treatment include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Further, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. The transformation of coryneform bacteria can be performed by, for example, the protoplast method (Gene, 39, 281-286 (1985)), the electroporation method (Bio/Technology, 7, 1067-1070(1989)), or the electric pulse method (Japanese Patent Laid-open (Kokai) No. 2-207791).

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or a parental strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase to, for example, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase to, for example, 1.5 times or more, 2 times or more, or 3 times or more of that of a non-modified strain.

The aforementioned methods for increasing the activity of a protein can be used for enhancement of the activities of arbitrary proteins such as L-amino acid biosynthesis enzymes, and enhancement of the expression of arbitrary genes such as genes encoding those arbitrary proteins, besides enhancement of the α-KG uptake carrier activity.

<1-4> Method for Reducing Activity of Protein

Hereafter, the methods for reducing the activity of a protein will be explained.

The expression "the activity of a protein is reduced" can mean that the activity of the protein is reduced as compared with a non-modified strain. Specifically, the expression "the activity of a protein is reduced" may mean that the activity of the protein per cell is reduced as compared with that of a non-modified strain. The term "non-modified strain" as used herein can refer to a strain that has not been modified so that the activity of an objective protein is reduced, and hence can be used as a control. The non-modified strain can also be referred to as "non-modified bacterium". Examples of the non-modified strain include a wild-type strain and/or a parental strain. Specific examples of the non-modified strain can include non-modified versions of the chosen bacterial strains, or similar strains, and can particularly include the exact strain of the coryneform bacterium. More specific examples of the non-modified strain include strains exemplified above, such as C. glutamicum ATCC 13032 and C. glutamicum ATCC 13869. That is, in an embodiment, the activity of a protein may be reduced as compared with the exact strain of bacteria, or it may be reduced as compared with a strain from the same species of bacteria, but not the exact strain. For example, if C. glutamicum ATCC 13869 is modified, the activity of a protein may be reduced as compared with the exact strain ATCC 13869, or it may be reduced as compared with a different strain of C. glutamicum, for example, C. glutamicum ATCC 13032.

The state that "the activity of a protein is reduced" also includes when the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes when the protein does not exist at all. When "the function of each molecule of the protein is reduced" can also include a when the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression the gene is reduced as compared with a non-modified strain such as a wild-type strain and parent strain. Specifically, the expression "the expression of a gene is reduced" may mean that the expression of the gene per cell is reduced as compared with that of a non-modified strain such as a wild-type strain or a parental strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, three or more nucleotides, of the expression control sequence are modified. For example, the transcription efficiency of a gene can be reduced by, for example, replacing the promoter of the gene on a chromosome with a weaker promoter. The term "weaker promoter" means a promoter providing an attenuated transcription of a gene compared with an inherently existing wild-type promoter of the gene. Examples of weaker promoters include, for example, inducible promoters. That is, an inducible promoter may function as a weaker promoter under a non-induced condition, such as in the absence of the corresponding inducer. Furthermore, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting a part or the whole of the coding region of the gene on a chromosome. Furthermore, the whole of a gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Furthermore, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region will usually more definitively inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, preparing a deficient gene modified so that it is unable to produce a protein that functions normally, and transforming a host with a recombinant DNA containing the deficient gene to cause homologous recombination between the deficient gene and the wild-type gene on a chromosome and thereby substitute the deficient gene for the wild-type gene on the chromosome. In this procedure, if a marker gene selected according to the characteristics of the host such as auxotrophy is included in the recombinant DNA, the operation becomes easier. Examples of the deficient gene include a gene including deletion of all or a part of the gene, gene including a missense mutation, gene including a nonsense mutation, gene including a frame shift mutation, and gene including insertion of a transposon or marker gene. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex having a plurality of subunits, a part or all of the plurality of subunits may be modified, so long as the activity of the protein is eventually reduced. That is, for example, a part or all of a plurality of genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA is preferably reduced to, for example, 50% or less, 20% or less, 10% or less, 5% or less, or 0%, of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein is preferably reduced to, for example, 50% or less, 20% or less, 10% or less, 5% or less, or 0%, of that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein as mentioned above can be applied to reduction in the activities of arbitrary proteins such as an enzyme that catalyzes a reaction branching away from the biosynthesis pathway of an objective L-amino acid to generate a compound other than the objective L-amino acid, and reduction in the expression of arbitrary genes such as genes encoding those arbitrary proteins.

<2> Method for Producing L-amino Acid of the Present Invention

The method of the present invention is a method for producing an L-amino acid by culturing the bacterium of the present invention in a medium, and collecting the L-amino acid from the medium. The L-amino acid to be produced is an L-amino acid of glutamate family. One kind of L-amino acid may be produced, or two or more kinds of L-amino acids may be produced.

The medium to be used is not particularly limited, so long as the bacterium can proliferate in it, and an objective L-amino acid can be produced. As the medium, for example, a usual medium used for culture of bacteria such as coryneform bacteria can be used. As the medium, for example, a medium containing carbon source, nitrogen source, phosphorus source, and sulfur source, as well as components selected from other various organic components and inorganic components as required can be used. Types and concentrations of the medium components can be appropriately determined according to various conditions such as the type of coryneform bacterium to be used.

Specific examples of the carbon source include, for example, saccharides such as glucose, fructose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, and aliphatic acids. As the carbon source, plant-derived materials can be preferably used. Examples of the plant include, for example, corn, rice, wheat, soybean, sugarcane, beet, and cotton. Examples of the plant-derived materials include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Further, xylose may be supplied by conversion from hexoses by, for example, imparting a pathway for converting hexose such as glucose to xylose to the bacterium of the present invention. As the carbon source, a single kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Furthermore, when an auxotrophic mutant that requires a nutrient such as amino acids for growth thereof is used, it is preferable to supply a required nutrient to the medium.

Furthermore, it is also preferable to, for example, restrict the amount of biotin in the medium, or add a surfactant or penicillin to the medium.

The culture conditions are not particularly limited so long as the bacterium can proliferate, and an objective L-amino acid can be produced. The culture can be performed, for example, under usual conditions used for culturing bacteria such as coryneform bacteria. The culture conditions can be appropriately set according to various conditions such as the type of coryneform bacterium to be used.

The culture can be performed by using a liquid medium. At the time of the culture, for example, the bacterium cultured on a solid medium such as agar medium may be directly inoculated into a liquid medium, or the bacterium cultured in a liquid medium as seed culture may be inoculated into a liquid medium for main culture. That is, the culture may be performed as separate seed culture and main culture. In such a case, the culture conditions of the seed culture and the main culture may be or may not be the same. Amount of the bacterium contained in the medium at the time of the start of the culture is not particularly limited. The main culture may be performed by, for example, inoculating a seed culture broth to a medium for main culture at an amount of 1 to 50% (v/v).

The culture can be performed as batch culture, fed-batch culture, continuous culture, or a combination of these. The medium used at the time of the start of the culture is also referred to as "starting medium". The medium supplied to a culture system (fermentation tank) in fed-batch culture or continuous culture is also referred to as "feed medium". Furthermore, to supply a feed medium to a culture system in fed-batch culture or continuous culture is also referred to as to "feed". Furthermore, when the culture is performed as separate seed culture and main culture, for example, both the seed culture and the main culture may be performed as batch culture. Alternatively, for example, the seed culture may be performed as batch culture, and the main culture may be performed as fed-batch culture or continuous culture.

The culture can be performed, for example, under aerobic conditions. The term "aerobic conditions" refers to conditions where the dissolved oxygen concentration in the liquid medium is not lower than 0.33 ppm, which is the detection limit for the detection with an oxygen membrane electrode, or may refer to a condition where the dissolved oxygen concentration in the liquid medium is not lower than 1.5 ppm. The oxygen concentration can be controlled to be, for example, 5 to 50%, or about 10%, of the saturated oxygen concentration. Specifically, the culture under an aerobic condition can be performed by aeration culture, shaking culture, stirring culture, or a combination thereof. pH of the medium may be, for example, 3 to 10, or 4.0 to 9.5. During the culture, pH of the medium can be adjusted as required.

pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., preferably 25 to 37° C. The culture period may be, for example, 10 to 120 hours. The culture may be continued, for example, until the carbon source contained in the medium is consumed, or until the bacterium loses the activity. By culturing the bacterium under such conditions as described above, an L-amino acid can be accumulated in the medium.

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated include, for example, pH 5.0 to 4.0, pH 4.5 to 4.0, 4.3 to 4.0, or around pH 4.0 (EP 1078989 A).

Production of an L-amino acid can be confirmed by known methods used for detection or identification of compounds. Examples of such methods include, for example, HPLC, LC/MS, GC/MS, and NMR. These methods can be independently used, or can be used in an appropriate combination.

The produced L-amino acid can be collected from the fermentation broth by known methods used for separation and purification of compounds. Examples of such methods include, for example, an ion-exchange resin method (Nagai, H. et al., Separation Science and Technology, 39(16), 3691-3710), precipitation, membrane separation (Japanese Patent Laid-open (Kokai) No. 9-164323 and Japanese Patent Laid-open (Kokai) No. 9-173792), and crystallization (WO2008/078448 and WO2008/078646). These methods can be independently used, or can be used in an appropriate combination. When the L-amino acid is accumulated in bacterial cells, the bacterial cells can be disrupted with, for example, ultrasonic waves or the like, and then the L-amino acid can be collected by the ion exchange resin method or the like from the supernatant obtained by removing the cells from the cell-disrupted suspension by centrifugation. The L-amino acid to be collected may be a free compound, a salt thereof, or a mixture thereof. Examples of the salt include, for example, sulfate, hydrochloride, carbonate, ammonium salt, sodium salt, and potassium salt. When L-glutamic acid is produced, L-glutamic acid to be collected may be free L-glutamic acid, sodium L-glutamate (monosodium L-glutamate, MSG), ammonium L-glutamate (monoammonium L-glutamate), or a mixture of these. For example, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5). The monosodium L-glutamate crystal can be used as, for example, an umami seasoning. The monosodium L-glutamate crystal may also be used as a seasoning in combination with a nucleic acid such as sodium guanylate (5'-GMP disodium salt) and sodium inosinate (5'-IMP disodium salt), which also have umami taste.

When the L-amino acid is precipitated in the medium, it can be collected by centrifugation, filtration, or the like. The L-amino acid precipitated in the medium may also be isolated together with the L-amino acid dissolving in the medium, after the L-amino acid dissolving in the medium is crystallized.

The collected L-amino acid may contain such components as bacterial cells, medium components, moisture, and by-product metabolites of the bacterium in addition to the L-amino acid. The collected L-amino acid may also be purified at a desired extent. Purity of the collected L-amino acid may be, for example, 50% (w/w) or higher, preferably 85% (w/w) or higher, particularly preferably 95% (w/w) or higher (JP1214636B, U.S. Pat. Nos. 5,431,933, 4,956,471, 4,777,051, 4,946,654, 5,840,358, 6,238,714, and US2005/0025878).

EXAMPLES

Hereafter, the present invention will be more specifically explained with reference to the following non-limiting examples.

Example: Glutamic Acid Production Culture Using Strain Having Enhanced Expression of kgtP Gene In this Example, glutamic acid production was performed by using a glutamic acid producing strain of *C. glutamicum* into which the kgtP gene derived from *E. coli* was introduced, and the effect of enhanced expression of kgtP gene on glutamic acid production was evaluated. kgtP gene is a gene encoding an α-ketoglutaric acid (α-KG) uptake carrier.

(1) Materials
Materials used in this Example are as follows.

TABLE 1

Primers used

| Primer | SEQ ID NO | Nucleotide Sequence (5'→3') |
|---|---|---|
| 1 | 1 | ccaagcttgcatgcctgcagaggaggattataatggctgaaagtactgtaac |
| 2 | 2 | cggtacccggggatccctaaagacgcatccccttcc |
| 3 | 3 | gaattcgagctcggtacccg |
| 4 | 4 | actggccgtcgttttacaac |
| 5 | 5 | aaaacgacggccagtacatcacaacagttcgctttg |
| 6 | 6 | accgagctcgaattcccgtgtttgaaaaagtatgttg |
| 7 | 15 | ctattctagaagcacaggaccgtttgccattgatattccccta |
| 8 | 16 | ctagtctagacggggtgctacgcgattaaaacatcaaacag |

<Plasmids Used>
pVK9
pVK9-kgtP
pVK9-BL_xfp
pVK9-kgtP-BL_xfp
<Strains Used>
*C. glutamicum* 2256ΔsucAΔldhA yggB*
*C. glutamicum* 2256ΔsucAΔldhA yggB*/pVK9
*C. glutamicum* 2256ΔsucAΔldhA yggB*/pVK9-kgtP
*C. glutamicum* 2256ΔsucAΔldhA yggB*/pVK9-BL_xfp
*C. glutamicum* 2256ΔsucAΔldhA yggB*/pVK9-kgtP-BL_xfp (2) Construction of Plasmids and Strains
<Construction of pVK9-kgtP>

PCR was performed using the genomic DNA of E. coli K-12 MG1655 (ATCC 47076) as the template, and primers 1 and 2, to amplify a DNA fragment containing the kgtP gene derived from E. coli (GenBank: U00096.3 kgtP-ORF (1299 bp)). The obtained DNA fragment was ligated to pVK9 (US2006-0141588) that had been digested with BamHI and PstI by using in-fusion (TaKaRa Inc.), to construct an expression plasmid of kgtP gene, pVK9-kgtP The nucleotide sequence of the kgtP gene of E. coli K-12 MG1655 and the amino acid sequence of the KgtP protein encoded by the gene are shown in SEQ ID NOS: 7 and 8, respectively.

<Construction of pVK9-BL_xfp>

PCR was performed using the genomic DNA of Bifidobacterium longum JCM1217 (ATCC 15707) as the template, and primers 7 and 8, to amplify a DNA fragment containing xfp gene derived from Bifidobacterium longum JCM1217 (ORF NO: BL0959). The obtained DNA fragment was digested with XbaI and ligated into the XbaI site of pVK9 by using T4 DNA ligase, to construct an expression plasmid of xfp gene, pVK9-BL_xfp. The nucleotide sequence of the xfp gene of Bifidobacterium longum JCM1217 and the amino acid sequence of the KgtP protein encoded by the gene are shown in SEQ ID NOS: 9 and 10, respectively.

<Construction of pVK9-kgtP-BL_xfp>

PCR was performed using the plasmid pVK9-kgtP constructed above as the template, and primers 3 and 4, to amplify a DNA fragment containing the vector and kgtP gene. Separately, PCR was performed using the plasmid pVK9-BL_xfp constructed above as the template, and primers 5 and 6, to amplify a DNA fragment containing the vector and xfp gene. The obtained two DNA fragments were ligated with each other by using in-fusion (TaKaRa Inc.), to construct a co-expression plasmid of kgtP gene and xfp gene, pVK9-kgtP-BL_xfp.

The plasmids each were introduced into C. glutamicum 2256ΔsucAΔldhA yggB* (WO2014/185430), to construct strains having an enhanced expression of kgtP gene and/or xfp gene. The strain 2256ΔsucAΔldhA yggB* is a glutamic acid producing strain derived from C. glutamicum 2256 (ATCC 13869). The strain 2256ΔsucAΔldhA yggB* is deficient in ldhA gene and sucA gene, and has an IS mutation (V419::IS) in yggB gene. The nucleotide sequence of this mutant yggB gene (V419::IS) and the amino acid sequence of the mutant YggB protein encoded by the gene are shown in SEQ ID NOS: 13 and 14, respectively.

(3) Glutamic Acid Production Culture

Glutamic acid production culture was performed by using each of the strains. The compositions of media used are shown in Table 2.

TABLE 2

| Media used | | |
|---|---|---|
| | Medium 1 | Medium 2 |
| Glucose | 80 g/L | 80 g/L |
| (NH$_4$)$_2$SO$_4$ | 30 g/L | 70 g/L |
| KH$_2$PO$_4$ | 1 g/L | 1 g/L |
| MgSO$_4$·7H$_2$O | 0.4 g/L | 0.4 g/L |
| FeSO$_4$·7H$_2$O | 0.01 g/L | 0.01 g/L |
| MnSO$_4$·5H$_2$O | 0.01 g/L | 0.01 g/L |
| VB$_1$ | 200 µg/L | 200 µg/L |
| Biotin | 60 µg/L | 0 µg/L |
| Mameno* | 0.48 g/L | 0.48 g/L |

The media having the aforementioned compositions and adjusted to pH8.0 with KOH were each prepared, and sterilized by autoclaving at 115° C. for 15 minutes. After the sterilization, CaCO$_3$ was added to the media in an amount of 50 g/L, and culture was performed.

*Mameno is soybean protein hydrolysate.

(3-1) Cultivation 1: Evaluation of Effect of Sole Enhancement of kgtP

Culture (i.e. preculture and main culture) was performed by using the aforementioned medium containing 50 g/L of CaCO$_3$ contained in large test tubes with shaking on a box shaker at 31.5° C. Firstly, the strains each were cultured in Medium 1 for 24 hr as preculture. Then, the obtained preculture broth was inoculated onto Medium 2, to perform main culture. A culture broth was sampled 23 hr after the inoculation. Residual glucose and glutamic acid were quantified by using Biotech Analyzer AS-310 (Sakura SI).

Results are shown in Table 3. By-production of α-KG was observed for the control strain 2256ΔsucAΔldhA yggB*/pVK9. By contrast, it was confirmed that the by-production amount of α-KG was decreased and accumulation of glutamic acid per consumed sugar (i.e. glutamic acid yield) was improved in the kgtP enhanced strain 2256ΔsucAΔldhA yggB*/pVK9-kgtP, as compared with the control strain. Therefore, it was considered that kgtP gene is a factor effective for glutamic acid production.

TABLE 3

Evaluation of effect of sole enhancement of kgtP

| | | amino acid production culture | | | |
|---|---|---|---|---|---|
| Host | plasmid | Glutamate (g/L) | Residual Glucose (g/L) | yield (%) | a-KG by-product (g/L) |
| 2256 ΔsucA ΔldhA yggB* | pVK9 | 37.07 | 0.0 | 46.3 | 1.52 |
| 2256 ΔsucA ΔldhA yggB* | pVK9-kgtP | 38.77 | 0.0 | 48.5 | 0.16 |

(3-2) Cultivation 2: Evaluation of Effect of Enhancement of kgtP in xfp Enhanced Strain Culture (i.e. preculture and main culture) was performed by using the aforementioned medium containing 50 g/L of CaCO$_3$ contained in large test tubes with shaking on a box shaker at 31.5° C. Firstly, the strains each were cultured in Medium 1 for 24 hr as preculture. Then, the obtained preculture broth was inoculated onto Medium 1, to perform main culture. A culture broth was sampled 16 hr after the inoculation. Residual glucose and glutamic acid were quantified by using Biotech Analyzer AS-310 (Sakura SI).

Results are shown in Table 4. It was confirmed that the by-production amount of α-KG was increased in the xfp enhanced strain 2256ΔsucAΔldhA yggB*/pVK9-BL_xfp, as compared with the control strain. By contrast, it was confirmed that the by-production amount of α-KG was decreased and accumulation of glutamic acid per consumed sugar (i.e. glutamic acid yield) was improved in the enhanced strain of both the kgtP and xfp genes, 2256ΔsucAΔldhA yggB*/pVK9-kgtP-BL_xfp, as compared with the xfp enhanced strain. Therefore, it was considered that kgtP gene is a factor effective for glutamic acid production also under xfp enhanced conditions.

TABLE 4

Evaluation of effect of enhancement of kgtP in xfp enhanced strain

| Host | plasmid | amino acid production culture | | | |
|---|---|---|---|---|---|
| | | Glutamate (g/L) | Residual Glucose (g/L) | yield (%) | a-KG by-product (g/L) |
| 2256 ΔsucA ΔldhA yggB* | pVK9 | 35.50 | 0.4 | 44.6 | 1.86 |
| 2256 ΔsucA ΔldhA yggB* | pVK9-BL_xfp | 38.95 | 1.4 | 49.6 | 2.61 |
| 2256 ΔsucA ΔldhA yggB* | pVK9-kgtP-BL_xfp | 39.00 | 2.9 | 50.6 | 1.87 |

EXPLANATION OF SEQUENCE LISTING

SEQ ID NOS:
1-6: Primers
7: Nucleotide sequence of kgtP gene of *Escherichia coli* K-12 MG1655
8: Amino acid sequence of KgtP protein of *Escherichia coli* K-12 MG1655
9: Nucleotide sequence of xfp gene of *Bifidobacterium longum* JCM1217
10: Amino acid sequence of Xfp protein of *Bifidobacterium longum* JCM1217
11: Nucleotide sequence of yggB gene of *Corynebacterium glutamicum* 2256 (ATCC 13869)
12: Amino acid sequence of YggB protein of *Corynebacterium glutamicum* 2256 (ATCC 13869)
13: Nucleotide sequence of mutant yggB gene (V419::IS) of *Corynebacterium glutamicum* 2256 (ATCC 13869)
14: Amino acid sequence of protein encoded by mutant yggB gene (V419::IS) of *Corynebacterium glutamicum* 2256 (ATCC 13869)
15 and 16: Primers

The invention claimed is:

1. A method for producing an L-amino acid, the method comprising:
   A) culturing a coryneform bacterium having an L-amino acid-producing ability in a medium; and
   B) collecting the L-amino acid from the medium, wherein the bacterium has been modified so that the activity of an α-ketoglutaric acid (α-KG) uptake carrier is increased as compared with a non-modified bacterium, wherein the α-KG uptake carrier is a protein encoded by kgtP gene, and
   wherein the L-amino acid is an L-amino acid of glutamate family.

2. The method according to claim 1, wherein the α-KG uptake carrier is a protein selected from the group consisting of:
   (a) a protein comprising the amino acid sequence of SEQ ID NO: 8;
   (b) a protein comprising the amino acid sequence of SEQ ID NO: 8, but which includes substitution, deletion, insertion, and/or addition of 1 to 10 amino acid residues, and wherein said protein has α-KG uptake activity; and
   (c) a protein comprising an amino acid sequence having an identity of 90% or higher to the amino acid sequence of SEQ ID NO: 8, and wherein said protein has α-KG uptake activity.

3. The method according to claim 1, wherein the activity of the α-KG uptake carrier is increased by increasing the expression of a gene encoding the α-KG uptake carrier.

4. The method according to claim 3, wherein the expression of the gene is increased by increasing the copy number of the gene and/or modifying an expression control sequence of the gene.

5. The method according to claim 1, wherein the bacterium has further been modified so that the activity of phosphoketolase is increased as compared with a non-modified bacterium.

6. The method according to claim 5, wherein the phosphoketolase comprises D-xylulose-5-phosphate phosphoketolase and/or fructose-6-phosphate phosphoketolase.

7. The method according to claim 5, wherein the activity of the phosphoketolase is increased by increasing the expression of a gene encoding the phosphoketolase.

8. The method according to claim 1, wherein the bacterium has further been modified so that the activity of α-ketoglutarate dehydrogenase and/or succinate dehydrogenase is reduced as compared with a non-modified bacterium.

9. The method according to claim 1, wherein the bacterium is a *Corynebacterium* bacterium.

10. The method according to claim 9, wherein the bacterium is *Corynebacterium glutamicum*.

11. The method according to claim 1, wherein the L-amino acid of glutamate family is selected from the group consisting of L-glutamic acid, L-glutamine, L-proline, L-arginine, L-citrulline, L-ornithine, and combinations thereof.

12. The method according to claim 1, wherein the L-amino acid of glutamate family is L-glutamic acid.

13. The method according to claim 11, wherein the L-glutamic acid is monoammonium L-glutamate or monosodium L-glutamate.

14. The method according to claim 12, wherein the bacterium has been further modified to harbor a mutant yggB gene.

15. The method according to claim 14, wherein the mutant yggB gene is a yggB gene having a mutation that improves the L-glutamic acid-producing ability of the coryneform bacterium.

16. The method according to claim 14, wherein the mutant yggB gene encodes a mutant YggB protein, and wherein said mutant yggB gene has a mutation selected from the group consisting of:
   (1) a mutation in the region coding for the amino acid residues at positions 419 to 533 of a wild-type YggB protein of SEQ ID NO: 12,
   (2) a mutation in the region coding for a transmembrane region of a wild-type YggB protein, and
   (3) a combination thereof.

17. The method according to claim 16, wherein the mutant YggB protein is a protein selected from the group consisting of:
   (a) a protein comprising the amino acid sequence of SEQ ID NO: 12, but which includes substitution, deletion, insertion, and/or addition of 1 to 10 amino acid residues, and wherein said protein is overexpressed in the coryneform bacterium, which provides an improved L-glutamic acid-producing ability of the coryneform bacterium; and (b) a protein comprising an amino acid sequence having an identity of 90% or higher to the amino acid sequence of SEQ ID NO: 12, and wherein said protein is overexpressed in the coryneform bacterium, which provides an improved L-glutamic acid-producing ability of the coryneform bacterium.

\* \* \* \* \*

```
SEQUENCE LISTING

<160> NUMBER OF SEQ ID NOS: 16

<210> SEQ ID NO 1
<211> LENGTH: 52
<212> TYPE: DNA
<213> ORGANISM: Artificial Sequence
<220> FEATURE:
<223> OTHER INFORMATION: primer

<400> SEQUENCE: 1
ccaagcttgc atgcctgcag aggaggatta taatggctga aagtactgta ac         52

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
cggtacccgg ggatccctaa agacgcatcc ccttcc                           36

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gaattcgagc tcggtacccg                                             20

<210> SEQ ID NO 4
<211> LENGTH: 20
<212> TYPE: DNA
<213> ORGANISM: Artificial Sequence
<220> FEATURE:
```

<223> OTHER INFORMATION: primer

<400> SEQUENCE: 4
actggccgtc gttttacaac         20

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
aaaacgacgg ccagtacatc acaacagttc gctttg         36

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
accgagctcg aattcccgtt ttgaaaaagt atgttg         36

<210> SEQ ID NO 7
<211> LENGTH: 1299
<212> TYPE: DNA
<213> ORGANISM: Escherichia coli

<400> SEQUENCE: 7

| atggctgaaa gtactgtaac ggcagacagc aaactgacaa gtagtgatac tcgtcgccgc | 60 |
| atttgggcga ttgtgggggc ctcttcaggt aatctggtcg agtggttcga tttctatgtc | 120 |
| tactcgttct gttcactcta ctttgcccac atcttcttcc cttccgggaa cacgacgact | 180 |
| caactactac aaacagcagg tgttttttgct gcgggattcc tgatgcgccc aataggcggt | 240 |
| tggctatttg ccgcatagc cgataaacat ggtcgcaaaa atcgatgct gttatcggtg | 300 |
| tgtatgatgt gtttcggatc gctggttatc gcctgcctcc caggttatga actataggt | 360 |
| acgtgggctc cggcattatt gcttctcgct cgtttatttc agggattatc tgttggcgga | 420 |
| gaatatggca ccagcgccac ctatatgagt gaagttgccg ttgaagggcg caaaggtttt | 480 |
| tacgcatcat ttcagtatgt gacgttgatc ggcggacaac tgctagccct actggttgtc | 540 |
| gtggttttac aacacaccat ggaagacgct gcactcagag agtggggatg gcgtattcct | 600 |
| ttcgcgttag gagctgtgtt agctgttgtg gcgttgtggt tacgtcgtca gttagatgaa | 660 |
| acttcgcaac aagaaacgcg cgcttttaaaa gaagctggat ctctgaaagg attatggcgc | 720 |
| aatcgccgtg cattcatcat ggttctcggt tttaccgctg cgggctccct ttgtttctat | 780 |
| accttcacta cttatatgca gaagtatctg gtaaatactg cgggaatgca tgccaacgtg | 840 |
| gcgagtggca ttatgactgc cgcattgttt gtattcatgc ttattcaacc actcattggc | 900 |
| gcgctgtcgg ataagattgg tcgccgtacc tcaatgttat gtttcggttc gctggcagcc | 960 |
| atttttaccg ttcctattct ctcagcattg caaaacgttt cctcgcctta tgccgctttt | 1020 |
| ggtctggtga tgtgtgccct gctgatagtg agtttttata catcaatcag tggaatactg | 1080 |
| aaggctgaga tgttcccggc acaggttcgc gcattaggcg ttggtctgtc atatgcggtc | 1140 |
| gctaatgcta tatttggtgg ttcggcgag tactagcgt tgtcgctgaa atcaatagga | 1200 |
| atggaaacag ccttcttctg gtatgtgacc ttgatggccg tggtggcgtt tctggtttct | 1260 | ttgatgctac atcgcaaagg gaaggggatg cgtctttag                                1299

<210> SEQ ID NO 8
<211> LENGTH: 432
<212> TYPE: PRT
<213> ORGANISM: Escherichia coli

<400> SEQUENCE: 8

Met Ala Glu Ser Thr Val Thr Ala Asp Ser Lys Leu Thr Ser Ser Asp
1               5                   10                  15

Thr Arg Arg Arg Ile Trp Ala Ile Val Gly Ala Ser Ser Gly Asn Leu
            20                  25                  30

Val Glu Trp Phe Asp Phe Tyr Val Tyr Ser Phe Cys Ser Leu Tyr Phe
        35                  40                  45

Ala His Ile Phe Phe Pro Ser Gly Asn Thr Thr Thr Gln Leu Leu Gln
    50                  55                  60

Thr Ala Gly Val Phe Ala Ala Gly Phe Leu Met Arg Pro Ile Gly Gly
65                  70                  75                  80

Trp Leu Phe Gly Arg Ile Ala Asp Lys His Gly Arg Lys Lys Ser Met
                85                  90                  95

Leu Leu Ser Val Cys Met Met Cys Phe Gly Ser Leu Val Ile Ala Cys
            100                 105                 110

Leu Pro Gly Tyr Glu Thr Ile Gly Thr Trp Ala Pro Ala Leu Leu Leu
        115                 120                 125

Leu Ala Arg Leu Phe Gln Gly Leu Ser Val Gly Gly Glu Tyr Gly Thr
    130                 135                 140

Ser Ala Thr Tyr Met Ser Glu Val Ala Val Glu Gly Arg Lys Gly Phe
145                 150                 155                 160

Tyr Ala Ser Phe Gln Tyr Val Thr Leu Ile Gly Gly Gln Leu Leu Ala
                165                 170                 175

Leu Leu Val Val Val Leu Gln His Thr Met Glu Asp Ala Ala Leu
            180                 185                 190

Arg Glu Trp Gly Trp Arg Ile Pro Phe Ala Leu Gly Ala Val Leu Ala
        195                 200                 205

Val Val Ala Leu Trp Leu Arg Arg Gln Leu Asp Glu Thr Ser Gln Gln
    210                 215                 220

Glu Thr Arg Ala Leu Lys Glu Ala Gly Ser Leu Lys Gly Leu Trp Arg
225                 230                 235                 240

Asn Arg Arg Ala Phe Ile Met Val Leu Gly Phe Thr Ala Ala Gly Ser
                245                 250                 255

Leu Cys Phe Tyr Thr Phe Thr Thr Tyr Met Gln Lys Tyr Leu Val Asn
            260                 265                 270

Thr Ala Gly Met His Ala Asn Val Ala Ser Gly Ile Met Thr Ala Ala
        275                 280                 285

Leu Phe Val Phe Met Leu Ile Gln Pro Leu Ile Gly Ala Leu Ser Asp
    290                 295                 300

Lys Ile Gly Arg Arg Thr Ser Met Leu Cys Phe Gly Ser Leu Ala Ala
305                 310                 315                 320

Ile Phe Thr Val Pro Ile Leu Ser Ala Leu Gln Asn Val Ser Ser Pro
                325                 330                 335

Tyr Ala Ala Phe Gly Leu Val Met Cys Ala Leu Leu Ile Val Ser Phe
            340                 345                 350

Tyr Thr Ser Ile Ser Gly Ile Leu Lys Ala Glu Met Phe Pro Ala Gln
        355                 360                 365

| Val | Arg | Ala | Leu | Gly | Val | Gly | Leu | Ser | Tyr | Ala | Val | Ala | Asn | Ala | Ile |
| | 370 | | | | 375 | | | | | 380 | | | | | |

| Phe | Gly | Gly | Ser | Ala | Glu | Tyr | Val | Ala | Leu | Ser | Leu | Lys | Ser | Ile | Gly |
| 385 | | | | | 390 | | | | | 395 | | | | | 400 |

| Met | Glu | Thr | Ala | Phe | Phe | Trp | Tyr | Val | Thr | Leu | Met | Ala | Val | Val | Ala |
| | | | | 405 | | | | | 410 | | | | | 415 | |

| Phe | Leu | Val | Ser | Leu | Met | Leu | His | Arg | Lys | Gly | Lys | Gly | Met | Arg | Leu |
| | | | 420 | | | | | 425 | | | | | 430 | | |

<210> SEQ ID NO 9
<211> LENGTH: 2478
<212> TYPE: DNA
<213> ORGANISM: Bifidobacterium longum

<400> SEQUENCE: 9

```
atgacgagtc ctgttattgg caccccttgg aagaagctca acgctccggt ttccgaggaa      60
gccctcgaag gcgttgacaa gtactggcgc gttgccaact accttccat cggccagatt     120
tatctgcgtt ccaacccgct gatgaaggag cccttcaccc gcgaagatgt gaagcaccgt     180
ctggtgggcc actggggcac tacccctggc ctgaacttcc tcatcggcca catcaaccgt     240
ttcattgctg accacggcca gaacaccgtg atcatcatgg gcccgggcca cggtggcccg     300
gccggtacct cccagtccta cctggacggc acctacaccg agaccttccc gaagatcacc     360
aaggacgaag ctggtctgca gaagttcttc cgtcagttct cttacccggg cggcattccg     420
tcccacttcg ctccggagac cccgggctcc atccacgagg tggtgagct gggttacgct     480
ctgtcccacg cttacggcgc catcatggac aacccgagcc tgtttgtccc ggccatcgtc     540
ggcgacggcg aggctgagac cggcccgctg gctaccggct ggcagtccaa caagctcgtg     600
aacccgcgca ccgacggtat cgtgctgccg atcctgcacc tcaacggcta caagatcgcc     660
aacccgacca tcctgtcccg catctccgac gaagagctcc acgagttctt ccacggcatg     720
ggttacgagc cctacgagtt cgtcgctggc ttcgatgatg aggaccacat gtccatccac     780
cgtcgcttcg ccgagctgtg ggagaccatc tgggacgaga tctgcgacat caaggccacc     840
gctcagaccg acaacgtgca ccgtccgttc tacccgatgc tgatcttccg cacccccgaag     900
ggctggacct gcccgaagta catcgacggc aagaagaccg agggctcctg gcgttcccac     960
caggtgccgc tggcttccgc ccgcgacacc gaggcccact tcgaggttct caagaactgg    1020
ctcgagtcct acaagccgga agagctgttc gacgccaacg tgctgtcaa ggacgacgtc    1080
cttgccttca tgccgaaggg cgagctgcgt atcggtgcca cccgaacgc caacggtggt    1140
gtgatccgca acgacctgaa gctgccgaac ctcgaggact acgaggtcaa ggaagtggct    1200
gagtacggcc acggctgggg ccagctcgag gccacccgta ccctgggtgc ctacactcgc    1260
gacatcatca gaacaaccc gcgcgacttc gcatcttcg gaccggatga accgcttcc    1320
aaccgtctgc aggcttccta cgaagtcacc aacaagcagt gggatgccgg ctacatctcc    1380
gacgaggtcg acgagcacat gcacgtctcc ggccaggtcg ttgagcagct gtccgagcac    1440
cagatggaag gcttcctcga ggcttacctg ctgaccggtc gtcacggcat ctggagctcc    1500
tacgagtcct tcgtccacgt gatcgactcc atgctgaacc agcacgccaa gtggcttgag    1560
gctaccgtcc gcgagattcc gtggcgcaag ccgattgcct ccatgaacct gctggtctcc    1620
tcccacgttt ggcgtcagga ccacaacggc ttctcccacc aggatcccgg tgtcacctcc    1680
gtcctgctga acaagtgctt ccacaacgac cacgtcatcg gcatctactt cgccaccgat    1740
```

```
gcgaacatgc tgctggccat cgccgagaag tgctacaagt ccaccaacaa gatcaacgcc    1800
atcatcgctg gtaagcagcc tgctgccacc tggctgaccc tggacgaggc tcgtgccgag    1860
ctcgagaagg gtgccgccgc ttgggattgg gcttccaccg ccaagaacaa cgatgaggcc    1920
gaggtcgtgc ttgccgccgc cggcgatgtc ccgactcagg agatcatggc tgcttccgac    1980
aagctgaagg aactgggcat caagttcaag gttgtgaacg ttgccgacct gctctccctg    2040
cagtccgcca aggagaacga cgaggctctg accgacgagg agttcgccga catcttcacc    2100
gccgacaagc cggtgctgtt cgcgtaccac tcctacgctc acgacgtgcg tggcctgatc    2160
tacgaccgtc cgaaccacga caacttcaac gtccacggct acgaggagga gggctccacc    2220
accaccccgt acgacatggt tcgtgtcaac cgcatcgacc gctacgagct gaccgctgag    2280
gctctgcgca tgatcgacgc cgacaagtac gccgacaaga tcgacgagct cgagaagttc    2340
cgtgatgagg ccttccagtt cgccgtcgac aacggctacg atcacccgga ctacaccgac    2400
tgggtgtact ccggcgtgaa caccgacaag aagggtgccg tcaccgctac cgccgctacc    2460
gctggcgaca acgagtga                                                   2478
```

<210> SEQ ID NO 10
<211> LENGTH: 825
<212> TYPE: PRT
<213> ORGANISM: Bifidobacterium longum

<400> SEQUENCE: 10

```
Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Phe Ile Ala Asp His Gly Gln Asn Thr Val Ile Met Gly Pro Gly
                85                  90                  95

His Gly Gly Pro Ala Gly Thr Ser Gln Ser Tyr Leu Asp Gly Thr Tyr
            100                 105                 110

Thr Glu Thr Phe Pro Lys Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240
```

-continued

Gly Tyr Glu Pro Tyr Glu Phe Val Ala Gly Phe Asp Asp Glu Asp His
                    245                 250                 255
Met Ser Ile His Arg Arg Phe Ala Glu Leu Trp Glu Thr Ile Trp Asp
            260                 265                 270
Glu Ile Cys Asp Ile Lys Ala Thr Ala Gln Thr Asp Asn Val His Arg
        275                 280                 285
Pro Phe Tyr Pro Met Leu Ile Phe Arg Thr Pro Lys Gly Trp Thr Cys
    290                 295                 300
Pro Lys Tyr Ile Asp Gly Lys Lys Thr Glu Gly Ser Trp Arg Ser His
305                 310                 315                 320
Gln Val Pro Leu Ala Ser Ala Arg Asp Thr Glu Ala His Phe Glu Val
                325                 330                 335
Leu Lys Asn Trp Leu Glu Ser Tyr Lys Pro Glu Glu Leu Phe Asp Ala
            340                 345                 350
Asn Gly Ala Val Lys Asp Val Leu Ala Phe Met Pro Lys Gly Glu
        355                 360                 365
Leu Arg Ile Gly Ala Asn Pro Asn Ala Asn Gly Val Ile Arg Asn
    370                 375                 380
Asp Leu Lys Leu Pro Asn Leu Glu Asp Tyr Glu Val Lys Glu Val Ala
385                 390                 395                 400
Glu Tyr Gly His Gly Trp Gln Leu Glu Ala Thr Arg Thr Leu Gly
                405                 410                 415
Ala Tyr Thr Arg Asp Ile Ile Lys Asn Asn Pro Arg Asp Phe Arg Ile
            420                 425                 430
Phe Gly Pro Asp Glu Thr Ala Ser Asn Arg Leu Gln Ala Ser Tyr Glu
    435                 440                 445
Val Thr Asn Lys Gln Trp Asp Ala Gly Tyr Ile Ser Asp Glu Val Asp
    450                 455                 460
Glu His Met His Val Ser Gly Gln Val Val Glu Gln Leu Ser Glu His
465                 470                 475                 480
Gln Met Glu Gly Phe Leu Glu Ala Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ala Ser Met Asn Leu Leu Val Ser Ser His Val Trp
    530                 535                 540
Arg Gln Asp His Asn Gly Phe Ser His Gln Asp Pro Gly Val Thr Ser
545                 550                 555                 560
Val Leu Leu Asn Lys Cys Phe His Asn Asp His Val Ile Gly Ile Tyr
                565                 570                 575
Phe Ala Thr Asp Ala Asn Met Leu Leu Ala Ile Ala Glu Lys Cys Tyr
            580                 585                 590
Lys Ser Thr Asn Lys Ile Asn Ala Ile Ile Ala Gly Lys Gln Pro Ala
        595                 600                 605
Ala Thr Trp Leu Thr Leu Asp Glu Ala Arg Ala Glu Leu Glu Lys Gly
    610                 615                 620
Ala Ala Ala Trp Asp Trp Ala Ser Thr Ala Lys Asn Asn Asp Glu Ala
625                 630                 635                 640
Glu Val Val Leu Ala Ala Ala Gly Asp Val Pro Thr Gln Glu Ile Met
                645                 650                 655
Ala Ala Ser Asp Lys Leu Lys Glu Leu Gly Ile Lys Phe Lys Val Val

```
                    660             665             670
Asn Val Ala Asp Leu Leu Ser Leu Gln Ser Ala Lys Glu Asn Asp Glu
            675                 680                 685

Ala Leu Thr Asp Glu Glu Phe Ala Asp Ile Phe Thr Ala Asp Lys Pro
        690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
                725                 730                 735

Glu Gly Ser Thr Thr Thr Pro Tyr Asp Met Val Arg Val Asn Arg Ile
            740                 745                 750

Asp Arg Tyr Glu Leu Thr Ala Glu Ala Leu Arg Met Ile Asp Ala Asp
        755                 760                 765

Lys Tyr Ala Asp Lys Ile Asp Glu Leu Glu Lys Phe Arg Asp Glu Ala
    770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asp Lys Lys Gly Ala Val Thr Ala
                805                 810                 815

Thr Ala Ala Thr Ala Gly Asp Asn Glu
            820                 825

<210> SEQ ID NO 11
<211> LENGTH: 1602
<212> TYPE: DNA
<213> ORGANISM: Corynebacterium glutamicum

<400> SEQUENCE: 11
atgattttag cgtacccat tcaatatttg ctctattcat tgtggaattg gattgtcgat      60
accggttttg atgtagcaat tatcctggtc ttggcgtttt tgattccacg tatcggccga     120
ctggccatgc gtattatcaa gcagcgagtg gagtctgcag ccgatgcgga caccactaag     180
aaccagctcg cgttcgctgg cgttggcgtt tatatcgcgc aaattgtggc gttttttcatg    240 cttgccgtct ccgcgatgca ggcttttggt ttctctctcg cgggcgctgc gattccggca     300
accattgcgt cagctgccat tggtcttggt gcgcagtcga ttgttgcgga cttcttggcc     360
ggatttttca tcctgacgga aaagcaattc ggcgtgggtg actgggtgcg ctttgagggc     420
aacggcatcg ttgttgaagg caccgtcatt gagatcacca tgcgcgcgac caaaattcgc     480
acgattgcac aagagaccgt gatcatcccg aactccacgg cgaaagtgtg catcaacaat     540
tctaataact ggtcgcgtgc ggttgtcgtt attccgatcc ccatgttggg ttctgaaaac     600
atcacagatg tcatcgcgcg ctctgaagct gcgactcgtc gcgcacttgg ccaggagaaa     660
atcgcaccgg aaatcctcgg tgaactcgat gtgcacccag ccacggaagt cacaccgcca     720
acggtggtcg gcatgccgtg gatggtcacc atgcgtttcc tcgtgcaagt caccgccggc     780
aatcaatggc tggtcgaacg cgccatccgc acagaaatca tcaacgaatt ctgggaagaa     840
tacggcagcg caaccactac atcgggaacc ctcattgatt ccttacacgt tgagcatgaa     900
gagccaaaga cctcgcttat cgacgcctcc ccccaggctc ttaaggaacc gaagccggag     960
gctgcggcga cggttgcatc gctagctgca tcgtctaacg acgatgcaga caatgcagac    1020
gcctcggcga tcaatgcagg caatccagag aaggaacttg attccgatgt gctggaacaa    1080
gaactctcca cgcgaagaacc ggaagaaaca gcaaaaccag atcactctct ccgaggcttc    1140
ttccgcactg attactaccc aaatcggtgg cagaagatcc tgtcgtttgg cggacgtgtc    1200
```

```
cgcatgagca cttccctgtt gttgggtgcg ctgctcttgc tgtcactatt taaggtcatg   1260
actgtggaac caagtgagaa ttggcaaaac tccagtggat ggctgtcacc aagcactgcc   1320
acctcaactg cggtgaccac ctccgaaact tccgcgccag caagcacgcc ttcgatgaca   1380
gtgcccacta cggtggagga gaccccaacg atggaatcta gcgtcgaaac gcagcaggaa   1440
acctcaaccc ctgcaaccgc aacgccccag cgagccgaca ccatcgaacc gaccgaggaa   1500
gccacgtcgc aggaggaaac gactgcatcg cagacgcagt ctccagcagt ggaagcacca   1560
accgcggtcc aagaaacagt tgcgccgacg tccaccccctt ag                    1602
```

<210> SEQ ID NO 12
<211> LENGTH: 533
<212> TYPE: PRT
<213> ORGANISM: Corynebacterium glutamicum

<400> SEQUENCE: 12

```
Met Ile Leu Gly Val Pro Ile Gln Tyr Leu Leu Tyr Ser Leu Trp Asn
  1               5                  10                  15

Trp Ile Val Asp Thr Gly Phe Asp Val Ala Ile Ile Leu Val Leu Ala
                 20                  25                  30

Phe Leu Ile Pro Arg Ile Gly Arg Leu Ala Met Arg Ile Ile Lys Gln
             35                  40                  45

Arg Val Glu Ser Ala Ala Asp Ala Asp Thr Thr Lys Asn Gln Leu Ala
         50                  55                  60

Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                 85                  90                  95

Ala Ile Pro Ala Thr Ile Ala Ser Ala Ile Gly Leu Gly Ala Gln
            100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
        130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300
```

```
Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Pro Glu
        355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Ala Ser Thr Pro Ser Met Thr Val Pro Thr Thr
    450                 455                 460

Val Glu Glu Thr Pro Thr Met Glu Ser Ser Val Glu Thr Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530

<210> SEQ ID NO 13
<211> LENGTH: 3063
<212> TYPE: DNA
<213> ORGANISM: Corynebacterium glutamicum
<220> FEATURE:
<221> NAME/KEY: CDS
<222> LOCATION: (1)..(1269)

<400> SEQUENCE: 13 atg att tta ggc gta ccc att caa tat ttg ctc tat tca ttg tgg aat     48
Met Ile Leu Gly Val Pro Ile Gln Tyr Leu Leu Tyr Ser Leu Trp Asn
1               5                   10                  15 tgg att gtc gat acc ggt ttt gat gta gca att atc ctg gtc ttg gcg     96
Trp Ile Val Asp Thr Gly Phe Asp Val Ala Ile Ile Leu Val Leu Ala
                20                  25                  30 ttt ttg att cca cgt atc ggc cga ctg gcc atg cgt att atc aag cag    144
Phe Leu Ile Pro Arg Ile Gly Arg Leu Ala Met Arg Ile Ile Lys Gln
            35                  40                  45 cga gtg gag tct gca gcc gat gcg gac acc act aag aac cag ctc gcg    192
Arg Val Glu Ser Ala Ala Asp Ala Asp Thr Thr Lys Asn Gln Leu Ala
    50                  55                  60 ttc gct ggc gtt ggc gtt tat atc gcg caa att gtg gcg ttt ttc atg    240
Phe Ala Gly Val Gly Val Tyr Ile Ala Gln Ile Val Ala Phe Phe Met
65                  70                  75                  80 ctt gcc gtc tcc gcg atg cag gct ttt ggt ttc tct ctc gcg ggc gct    288
Leu Ala Val Ser Ala Met Gln Ala Phe Gly Phe Ser Leu Ala Gly Ala
```

-continued

|  |  |  |  |  |  |  |  |  |  |  |  |  |  |  |  |  |
|---|---|---|---|---|---|---|---|---|---|---|---|---|---|---|---|---|
|  |  |  |  | 85 |  |  |  | 90 |  |  |  | 95 |  |  |  |  |
| gcg | att | ccg | gca | acc | att | gcg | tca | gct | gcc | att | ggt | ctt | ggt | gcg | cag | 336 |
| Ala | Ile | Pro | Ala | Thr | Ile | Ala | Ser | Ala | Ala | Ile | Gly | Leu | Gly | Ala | Gln |  |
|  |  |  | 100 |  |  |  |  | 105 |  |  |  |  | 110 |  |  |  |
| tcg | att | gtt | gcg | gac | ttc | ttg | gcc | gga | ttt | ttc | atc | ctg | acg | gaa | aag | 384 |
| Ser | Ile | Val | Ala | Asp | Phe | Leu | Ala | Gly | Phe | Phe | Ile | Leu | Thr | Glu | Lys |  |
|  |  | 115 |  |  |  |  | 120 |  |  |  |  | 125 |  |  |  |  |
| caa | ttc | ggc | gtg | ggt | gac | tgg | gtg | cgc | ttt | gag | ggc | aac | ggc | atc | gtt | 432 |
| Gln | Phe | Gly | Val | Gly | Asp | Trp | Val | Arg | Phe | Glu | Gly | Asn | Gly | Ile | Val |  |
| 130 |  |  |  |  | 135 |  |  |  |  | 140 |  |  |  |  |  |  |
| gtt | gaa | ggc | acc | gtc | att | gag | atc | acc | atg | cgc | gcg | acc | aaa | att | cgc | 480 |
| Val | Glu | Gly | Thr | Val | Ile | Glu | Ile | Thr | Met | Arg | Ala | Thr | Lys | Ile | Arg |  |
| 145 |  |  |  |  | 150 |  |  |  |  | 155 |  |  |  |  | 160 |  |
| acg | att | gca | caa | gag | acc | gtg | atc | atc | ccg | aac | tcc | acg | gcg | aaa | gtg | 528 |
| Thr | Ile | Ala | Gln | Glu | Thr | Val | Ile | Ile | Pro | Asn | Ser | Thr | Ala | Lys | Val |  |
|  |  |  |  | 165 |  |  |  |  | 170 |  |  |  |  | 175 |  |  |
| tgc | atc | aac | aat | tct | aat | aac | tgg | tcg | cgt | gcg | gtt | gtc | gtt | att | ccg | 576 |
| Cys | Ile | Asn | Asn | Ser | Asn | Asn | Trp | Ser | Arg | Ala | Val | Val | Val | Ile | Pro |  |
|  |  |  | 180 |  |  |  |  | 185 |  |  |  |  | 190 |  |  |  |
| atc | ccc | atg | ttg | ggt | tct | gaa | aac | atc | aca | gat | gtc | atc | gcg | cgc | tct | 624 |
| Ile | Pro | Met | Leu | Gly | Ser | Glu | Asn | Ile | Thr | Asp | Val | Ile | Ala | Arg | Ser |  |
|  |  | 195 |  |  |  |  | 200 |  |  |  |  | 205 |  |  |  |  |
| gaa | gct | gcg | act | cgt | cgc | gca | ctt | ggc | cag | gag | aaa | atc | gca | ccg | gaa | 672 |
| Glu | Ala | Ala | Thr | Arg | Arg | Ala | Leu | Gly | Gln | Glu | Lys | Ile | Ala | Pro | Glu |  |
| 210 |  |  |  |  | 215 |  |  |  |  | 220 |  |  |  |  |  |  |
| atc | ctc | ggt | gaa | ctc | gat | gtg | cac | cca | gcc | acg | gaa | gtc | aca | ccg | cca | 720 |
| Ile | Leu | Gly | Glu | Leu | Asp | Val | His | Pro | Ala | Thr | Glu | Val | Thr | Pro | Pro |  |
| 225 |  |  |  |  | 230 |  |  |  |  | 235 |  |  |  |  | 240 |  |
| acg | gtg | gtc | ggc | atg | ccg | tgg | atg | gtc | acc | atg | cgt | ttc | ctc | gtg | caa | 768 |
| Thr | Val | Val | Gly | Met | Pro | Trp | Met | Val | Thr | Met | Arg | Phe | Leu | Val | Gln |  |
|  |  |  |  | 245 |  |  |  |  | 250 |  |  |  |  | 255 |  |  |
| gtc | acc | gcc | ggc | aat | caa | tgg | ctg | gtc | gaa | cgc | gcc | atc | cgc | aca | gaa | 816 |
| Val | Thr | Ala | Gly | Asn | Gln | Trp | Leu | Val | Glu | Arg | Ala | Ile | Arg | Thr | Glu |  |
|  |  |  | 260 |  |  |  |  | 265 |  |  |  |  | 270 |  |  |  |
| atc | atc | aac | gaa | ttc | tgg | gaa | gaa | tac | ggc | agc | gca | acc | act | aca | tcg | 864 |
| Ile | Ile | Asn | Glu | Phe | Trp | Glu | Glu | Tyr | Gly | Ser | Ala | Thr | Thr | Thr | Ser |  |
|  |  | 275 |  |  |  |  | 280 |  |  |  |  | 285 |  |  |  |  |
| gga | acc | ctc | att | gat | tcc | tta | cac | gtt | gag | cat | gaa | gag | cca | aag | acc | 912 |
| Gly | Thr | Leu | Ile | Asp | Ser | Leu | His | Val | Glu | His | Glu | Glu | Pro | Lys | Thr |  |
| 290 |  |  |  |  | 295 |  |  |  |  | 300 |  |  |  |  |  |  |
| tcg | ctt | atc | gac | gcc | tcc | ccc | cag | gct | ctt | aag | gaa | ccg | aag | ccg | gag | 960 |
| Ser | Leu | Ile | Asp | Ala | Ser | Pro | Gln | Ala | Leu | Lys | Glu | Pro | Lys | Pro | Glu |  |
| 305 |  |  |  |  | 310 |  |  |  |  | 315 |  |  |  |  | 320 |  |
| gct | gcg | gcg | acg | gtt | gca | tcg | cta | gct | gca | tcg | tct | aac | gac | gat | gca | 1008 |
| Ala | Ala | Ala | Thr | Val | Ala | Ser | Leu | Ala | Ala | Ser | Ser | Asn | Asp | Asp | Ala |  |
|  |  |  |  | 325 |  |  |  |  | 330 |  |  |  |  | 335 |  |  |
| gac | aat | gca | gac | gcc | tcg | gcg | atc | aat | gca | ggc | aat | cca | gag | aag | gaa | 1056 |
| Asp | Asn | Ala | Asp | Ala | Ser | Ala | Ile | Asn | Ala | Gly | Asn | Pro | Glu | Lys | Glu |  |
|  |  |  | 340 |  |  |  |  | 345 |  |  |  |  | 350 |  |  |  |
| ctt | gat | tcc | gat | gtg | ctg | gaa | caa | gaa | ctc | tcc | agc | gaa | gaa | ccg | gaa | 1104 |
| Leu | Asp | Ser | Asp | Val | Leu | Glu | Gln | Glu | Leu | Ser | Ser | Glu | Glu | Pro | Glu |  |
|  |  | 355 |  |  |  |  | 360 |  |  |  |  | 365 |  |  |  |  |
| gaa | aca | gca | aaa | cca | gat | cac | tct | ctc | cga | ggc | ttc | ttc | cgc | act | gat | 1152 |
| Glu | Thr | Ala | Lys | Pro | Asp | His | Ser | Leu | Arg | Gly | Phe | Phe | Arg | Thr | Asp |  |
| 370 |  |  |  |  | 375 |  |  |  |  | 380 |  |  |  |  |  |  |
| tac | tac | cca | aat | cgg | tgg | cag | aag | atc | ctg | tcg | ttt | ggc | gga | cgt | gtc | 1200 |
| Tyr | Tyr | Pro | Asn | Arg | Trp | Gln | Lys | Ile | Leu | Ser | Phe | Gly | Gly | Arg | Val |  |
| 385 |  |  |  |  | 390 |  |  |  |  | 395 |  |  |  |  | 400 |  |
| cgc | atg | agc | act | tcc | ctg | ttg | ttg | ggt | gcg | ctg | ctc | ttg | ctg | tca | cta | 1248 |

```
Arg Met Ser Thr Ser Leu Leu Leu Gly Ala Leu Leu Leu Ser Leu
            405                 410                 415 ttt aag ggg ctc ttc ctg ttt tagagtgcat tgatcttatg gaccaactgc      1299
Phe Lys Gly Leu Phe Leu Phe
            420 cctgaatgga taaggcaccg cagaatgtag tggttcaaat tacggaaacc tagagcaatc  1359 ccacgcaaat gctccaaccg tccgttgatc gcttcgaccg gaccgttgga gacaccaaca  1419 tcgaaatacg ccaacacatc accaagtcgt taaacaaac tacgacccaa ctgcgcgagt   1479 tccttattcg gccccttcaa cacccgaagc tgatcaataa tggtccgcat tttcttcttc  1539 gcttcacgct tattacccat ctgataacaa tcaataatcg cctgatacgc aagccacgca  1599 agctttaaca ccccgtagtc tttgtcatac gcccacaact gctccaagct tcttgctga   1659 cgaggactca accacttgtg cgtggtcaac aaggtcttcc ggttttata caacggatcc   1719 tggcttaaac cacgacgctg gtatttctcc cgctggaggc gttgccggca ggcggtgagc  1779 ttgtcaccag caagccgcac aacatggaat ggatccatca cgcgacgagc agaaggaatg  1839 agttctttac ttgctgtggc gtagccttgg aacccatcca tggacacgat ccgtatctga  1899 ttgcggaact gttcaccgcg ggaaccaagc caggaccgta agcatcagc actacgacct   1959 gggacgacat ctaataaccg ggcaggacac cgtgagtcat accgatgccc ggtcatatcg  2019 acaatcacgg tgacaaaccc atcaccatgc ttagccctat tatgtgacca cttatgctca  2079 tccaccccaa tgacatacac tccatcaaga tggtgaggat cgttatagac cagctcacgg  2139 cacatatcga gggctagttg gcaggttaaa tcccaccctaa gcccaagtgc tttcgcggtt  2199 gcgtgaacac tcatccggtc aatagcaagg cgttgcaaaa tccagcgggt gacccggtgg  2259 gtgaccttt taccgtggtc agcgcagctt agttctgctt ggaaatactt ttgcttacat   2319 gtcgggttgg tgcagcggta gcgaggtaga cggataaaca gtttggtggg aaacccgacg  2379 atgggtaaat caatgagcat ccggtgggtg tgatgacgaa acaccccagg ttgggagcat  2439 tctgggcagg tggaggtata gtcgagtgcg tctgcttcga tcagggtgta atcacctgca  2499 tcggaagcgc cggtgatggt gagtcctagt tccgcagtgc ggcagatggt gtcagcgatg  2559 atgttgccgg tagacttcat gggtagagcc ttttgttggt gtttggttag cttagatacc  2619 taaaccttaa ccctgacaaa aggctcgttt atttttcgggt ctacaccgct agcccaggtt  2679 ctgtgatgta ccccaaaacc ggaagggcca tttaaggtca tgactgtgga accaagtgag  2739 aattggcaaa actccagtgg atggctgtca ccaagcactg ccacctcaac tgcggtgacc  2799 acctccgaaa cttccgcgcc agcaagcacg ccttcgatga cagtgcccac tacggtggag  2859 gagaccccaa cgatggaatc tagcgtcgaa acgcagcagg aaacctcaac ccctgcaacc  2919 gcaacgcccc agcgagccga caccatcgaa ccgaccgagg aagccacgtc gcaggaggaa  2979 acgactgcat cgcagacgca gtctccagca gtggaagcac caaccgcggt ccaagaaaca  3039 gttgcgccga cgtccacccc ttag                                         3063
```

<210> SEQ ID NO 14
<211> LENGTH: 423
<212> TYPE: PRT
<213> ORGANISM: Corynebacterium glutamicum

<400> SEQUENCE: 14

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala

```
            20                  25                  30
Phe Leu Ile Pro Arg Ile Gly Arg Leu Ala Met Arg Ile Ile Lys Gln
            35                  40                  45

Arg Val Glu Ser Ala Ala Asp Ala Asp Thr Thr Lys Asn Gln Leu Ala
 50                  55                  60

Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                    85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
            130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                    165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
            210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                    245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Ala
                    325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                    405                 410                 415

Phe Lys Gly Leu Phe Leu Phe
            420

<210> SEQ ID NO 15
```

```
<211> LENGTH: 43
<212> TYPE: DNA
<213> ORGANISM: Artificial Sequence
<220> FEATURE:
<223> OTHER INFORMATION: primer

<400> SEQUENCE: 15
ctattctaga agcacaggac cgtttgccat tgatattccc cta                             43

<210> SEQ ID NO 16
<211> LENGTH: 42
<212> TYPE: DNA
<213> ORGANISM: Artificial Sequence
<220> FEATURE:
<223> OTHER INFORMATION: primer

<400> SEQUENCE: 16
ctagtctaga cggggtgcta cgcgattaaa acatcacaac ag                              42
```